(12) United States Patent
O'Hare et al.

(10) Patent No.: US 8,933,135 B2
(45) Date of Patent: Jan. 13, 2015

(54) PROCESS FOR PRODUCING METHANOL

(75) Inventors: Dermot O'Hare, Oxford (GB); Andrew Ashley, Oxford (GB)

(73) Assignee: ISIS Innovation Limited, Summertown (GB)

( * ) Notice: Subject to any disclaimer, the term of this patent is extended or adjusted under 35 U.S.C. 154(b) by 325 days.

(21) Appl. No.: 13/501,476

(22) PCT Filed: Oct. 14, 2010

(86) PCT No.: PCT/GB2010/051733
§ 371 (c)(1),
(2), (4) Date: Jun. 26, 2012

(87) PCT Pub. No.: WO2011/045605
PCT Pub. Date: Apr. 21, 2011

(65) Prior Publication Data
US 2012/0283340 A1    Nov. 8, 2012

(30) Foreign Application Priority Data
Oct. 14, 2009    (GB) .................................. 0917999.5

(51) Int. Cl.
C07C 27/00    (2006.01)
C07C 29/153    (2006.01)
C07C 29/159    (2006.01)

(52) U.S. Cl.
CPC ............. *C07C 29/153* (2013.01); *C07C 29/159* (2013.01)
USPC ........................................................... 518/700

(58) Field of Classification Search
CPC ...... C07C 29/153; C07C 31/04; C07C 29/159
USPC ........................................................... 518/700
See application file for complete search history.

(56) References Cited

PUBLICATIONS

Chinese Abstract CN 101690894 A, Apr. 2010.*
PCT Search Report/Written Opinion prepared for PCT/GB2010/051733, mailed Feb. 10, 2011.
United Kingdom Search Report prepared for GB0917999.5, search prepared Feb. 16, 2010.

* cited by examiner

*Primary Examiner* — Jafar Parsa
(74) *Attorney, Agent, or Firm* — Barnes & Thornburg LLP

(57) ABSTRACT

The present invention relates to a novel process for the production of methanol. The process comprises the heterolytic cleavage of hydrogen by a frustrated Lewis pair comprising a Lewis acid and a Lewis base; and the hydrogenation of $CO_2$ with the heterolytically cleaved hydrogen to form methanol.

19 Claims, 2 Drawing Sheets

(a)    (b)

PROCESS FOR PRODUCING METHANOL

CROSS-REFERENCE TO RELATED APPLICATIONS

This application is a U.S. national counterpart application of PCT International Application Ser. No. PCT/GB2010/051733, filed Oct. 14, 2010, which claims priority to United Kingdom Patent Application Ser. No. 0917999.5, filed Oct. 14, 2009, the disclosures of both which are hereby incorporated herein by reference.

This invention relates to a novel process for the production of methanol. More specifically, the present invention relates to a process of producing methanol by the hydrogenation of carbon dioxide ($CO_2$).

BACKGROUND

The role of carbon dioxide as a greenhouse gas and its contribution to global warming is widely recognised by both scientists and governmental agencies. It is now imperative that new reactions and processes are discovered that can either efficiently store or utilise the abundant and renewable $CO_2$ resource in an environmentally friendly manner. However, this presents a fundamental challenge because carbon dioxide is kinetically and thermodynamically stable.

The storage of the non polar $CO_2$ molecule in a solid form is difficult, but progress is being made using a range of high surface area macro and microporous materials, such as inorganic materials (e.g. alumina, silicas and zeolites), organic materials (e.g. activated carbons), as well as complex metal-organic frameworks (MOFs).[1] Arguably a more desirable outcome would be the low temperature conversion of $CO_2$ into alternative chemicals useful for both energy production and as chemical feedstocks. Simultaneously this would have the additional benefit of reducing our requirements on fossil fuel reserves. Homogenous and heterogeneous processes have been developed that utilise $CO_2$ to produce CO, formic acid and its derivatives.[2] However, these reactions are far from ideal, so further breakthrough technologies are required.

There is particular interest in the reduction of $CO_2$ by $H_2$ to give renewable sources such as methanol. Methanol is considered to be a valuable product because it can be safely stored and transported. In addition, world demand for methanol is currently increasing enormously because of its role as a precursor to many useful organic chemicals (e.g., formaldehyde, acetic acid); a substitute for traditional fossil fuels; and in the generation of electricity in fuel cells.

$CO_2$ hydrogenation has been extensively developed using solid oxide catalysts, but was only first reported in homogeneous solution by Sasaki and co-workers using $Ru_3(CO)_{12}$—KI mixtures.[3] However, these systems tend to give distributions of $C_1$ products, namely CO, $CH_3OH$ and $CH_4$.

Furthermore, the transition metal oxide catalysts used in these hydrogenation reactions can be expensive, and their toxicity can also give rise to potential environmental and/or disposal problems.

Accordingly, there is a need for improved processes for the manufacture methanol from $CO_2$ which can: (i) provide the methanol in a pure form (i.e. without other $C_1$ by-products); (ii) be operated at relatively low temperatures and pressures; and (iii) avoid the use of transition metal catalysts.

BRIEF SUMMARY OF THE DISCLOSURE

In a first aspect, the present invention provides a process for the preparation of methanol comprising:
(i) the heterolytic cleavage of hydrogen by a frustrated Lewis pair comprising a Lewis acid and a Lewis base; and
(ii) the hydrogenation of $CO_2$ with the heterolytically cleaved hydrogen formed in step (i) to form methanol.

In addition to the obvious advantages associated with a process that utilises the abundant $CO_2$ resource available, the process of the present invention also avoids the use of metallic catalysts. Furthermore, the reaction can proceed at relatively low temperatures and pressures, and it is also specific for the production of methanol (i.e. no other $C_1$ by-products are formed).

The process of the present invention makes use of the ability of a frustrated Lewis pair to heterolytically cleave hydrogen. Various researchers have shown that frustrated Lewis pairs can heterolytically activate hydrogen,[4] and that these systems can then be subsequently used in the metal-free catalytic hydrogenation of olefins and other organic substrates.[5]

However, no one has used these systems to catalytically hydrogenate $CO_2$ and thereby provide an advantageous method for the synthesis of methanol.

In a further aspect, the present invention provides the use of a frustrated Lewis pair in a process as defined above.

The present invention also provides, in a further aspect, methanol obtainable by, or obtained by, or directly obtained by a process defined herein.

DETAILED DESCRIPTION

Definitions

Hydrocarbyl

The term "hydrocarbyl" as used herein includes reference to moieties consisting exclusively of hydrogen and carbon atoms; such a moiety is typically an aliphatic moiety. The moiety may, for example, comprise 1, 2, 3, 4, 5, 6, 7, 8, 9, 10, 11 or 12 carbon atoms. Examples of hydrocarbyl groups include (1-6C)alkyl (e.g. $C_1$, $C_2$, $C_3$ or $C_4$ alkyl, for example methyl, ethyl, propyl, isopropyl, n-butyl, sec-butyl or tert-butyl); (2-6C)alkenyl (e.g. 2-butenyl); and (2-6C)alkynyl (e.g. 2-butynyl) and the like.

Alkyl

The term "alkyl" as used herein include reference to a straight or branched chain alkyl moieties, typically having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, an alkyl may have 1, 2, 3 or 4 carbon atoms.

Alkoxy

The term "alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9 or 10 ring carbon atoms. In particular, carbocyclyl includes a 3- to 10-membered ring or ring system and, in particular, a 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, naphthyl, and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9 or 10 ring carbon atoms. Aryl is often phenyl but may be a polycyclic ring system, having two or more rings, at least one of which is aromatic. This term includes reference to groups such as phenyl, naphthyl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9 or 10 ring atoms, at least one of which is selected from nitrogen, oxygen, phosphorus, silicon and sulphur. In particular, heterocyclyl includes a 5- to 10-membered ring or ring system and more particularly a 5- or 6-membered ring, which may be saturated or unsaturated.

A heterocyclic moiety is, for example, selected from imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heteroaryl

The term "heteroaryl" as used herein includes reference to an aromatic heterocyclic ring system having 5, 6, 7, 8, 9 or 10 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" or "halo" as used herein includes reference to F, Cl, Br or I. In a particular, halogen may be F or Cl, of which F is more common.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Frustrated Lewis Pair

The term "frustrated Lewis pair" is used herein to refer to a compound or mixture of compounds containing a Lewis acid and a Lewis base which, because of steric hindrance, cannot combine to form a strongly bound adduct, or may not in fact form any adduct at all. The frustrated Lewis pairs of the present invention must be capable of heterolytically cleaving hydrogen.

Optionally Substituted Ferrocene

The expression "optionally substituted ferrocene" used herein refers to two cyclopentadienyl rings with a central Fe atom. The rings may be substituted with hydrocarbyl, aryl, heterocyclyl etc, and/or may further comprise a (2-3C) bridge that links the two cyclopentadienyl rings, which may also be optionally substituted with (1-4C)alkyl. The N or P atom of a Lewis base as defined herein may be bonded to the cyclopentadienyl rings or the bridge group connecting the two cyclopentadienyl rings.

As previously stated, the present invention provides a process for the preparation of methanol comprising:

(i) the heterolytic cleavage of hydrogen by a frustrated Lewis pair; and (ii) the hydrogenation of $CO_2$ with the heterolytically cleaved hydrogen formed in step (i) to yield the methanol product.

Frustrated Lewis Pair

Any suitable frustrated Lewis pair that can heterolytically cleave hydrogen can be used in the process of the present invention.

In an embodiment of the invention, the Lewis acid and Lewis base are separate molecules that together form a frustrated Lewis pair.

In an alternative embodiment, the Lewis acid and Lewis base may be separate moieties of the same molecule. In other words, the Lewis acid and Lewis base may be linked together to form a single molecule. The precise nature of the linker that connects the Lewis acid to the Lewis Base is not critical as long as the Lewis acid and Lewis base moieties can still perform their function by interacting with, and heterolytically cleaving, hydrogen.

In a further embodiment, the frustrated Lewis pair is immobilised onto a suitable solid support (this could be a either an organic (polymer-based) or inorganic solid phase). The immobilisation on a solid support may be facilitated by covalently bonding to otherwise adhering the separate Lewis acid or Lewis base molecules to the solid support, or by linking a single molecule that comprises suitable Lewis acid and Lewis base moieties to the solid support.

(i) Lewis Acids

It will be appreciated that any suitable Lewis acid known in the art as a component of a frustrated Lewis pair which is capable of cleaving $H_2$ is encompassed by the present invention.

Particularly suitable Lewis acids are of the structural formula I shown below:

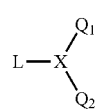

wherein:

X is a Group 13 element such as B or Al;

$Q_1$ and $Q_2$ are each independently selected from hydrocarbyl, carbocyclyl, or heterocyclyl, each of which is optionally substituted with one or more substituents selected from halo, cyano, nitro, hydroxyl, (1-6C)alkyl, (3-6C)cycloalkyl, (1-6C)alkoxy, phenyl, (1-6C)alkylphenyl, heterocyclyl, (1-6C)alkylheterocyclyl, or a linker group which is capable of binding the X atom to a solid support; and L is hydrogen, halo, any one of the groups defined above for $Q_1$ or $Q_2$, or a linker group which is capable of binding the X atom to a solid support.

In an embodiment, X is selected from boron or aluminium.

In an embodiment, X is boron.

In an embodiment, X is aluminium.

In an embodiment, $Q_1$ and $Q_2$ are each independently selected from $C_{1-12}$alkyl, phenyl, naphthyl, heteroaryl, each of which is substituted by one or more substituent groups selected from halo, cyano, nitro, (1-6C)alkyl or (1-6C)alkoxy.

In a further embodiment, $Q_1$ and $Q_2$ are each independently phenyl or pyrrolyl, each of which is substituted by one or more substituent groups selected from halo, cyano, nitro, (1-6C)alkyl or (1-6C) alkoxy.

In a further embodiment, $Q_1$ and $Q_2$ are phenyl substituted by halo, cyano, nitro or (1-6C)alkoxy.

In a further embodiment, $Q_1$ and $Q_2$ are each independently phenyl or heteroaryl substituted by an electron withdrawing substituent.

In a further embodiment, $Q_1$ and $Q_2$ are each independently phenyl or heteroaryl substituted by three to five electron withdrawing substituents.

In a further embodiment, $Q_1$ and $Q_2$ are each independently phenyl or heteroaryl substituted by one or more halo, cyano, nitro, or (1-6C) alkoxy groups.

In a further embodiment, $Q_1$ and $Q_2$ are each independently phenyl or heteroaryl substituted by three to five halo, cyano, or nitro groups.

In an embodiment, L is any one of the groups defined herein for $Q_1$ or $Q_2$.

When L is a linker group, it may be any suitable linker group capable of connecting the boron atom of the Lewis acid to a solid support. For example, it may be a functional group capable of reacting with a functional group on the solid support surface to form a covalent bond, or it may be a hydrocarbyl, carbocyclyl, heterocyclyl group which is substituted with a substituent comprising a suitable functional group. The solid this could be a either an organic (polymer-based) or inorganic solid phase.

In a particular embodiment, groups $Q_1$, $Q_2$ and L are the same.

In a further embodiment, the Lewis acid has the structural formula II shown below:

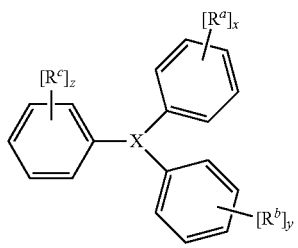

II wherein:
X is as defined above;
$R^a$, $R^b$ and $R^c$ are each independently selected from halo, cyano, nitro, hydroxy, amino, (1-6C)alkyl, (3-6C)cycloalkyl, (1-6C)alkoxy, phenyl, (1-6C)alkylphenyl; and x, y and z are each independently selected from 0, 1, 2, 3, 4 or 5.

In an alternative embodiment, $R^a$, $R^b$ and $R^c$ are each electron withdrawing substituents.

In an embodiment, $R^a$, $R^b$ and $R^c$ are each independently selected from halo, cyano, nitro, or (1-4C)alkoxy.

In an embodiment, $R^a$, $R^b$ and $R^c$ are each independently selected from halo, cyano, nitro, (1-4C)alkyl, (1-4C)alkoxy, phenyl, or (1-2C)alkylphenyl.

In an embodiment, $R^a$, $R^b$ and $R^c$ are each independently selected from halo, cyano, nitro, (1-4C)alkyl, or (1-4C)alkoxy.

In a particular embodiment, $R^a$, $R^b$ and $R^c$ are each independently selected from chloro, fluoro or cyano.

In a further embodiment, $R^a$, $R^b$ and $R^c$ are each independently selected from fluoro or cyano.

In a further embodiment, $R^a$, $R^b$ and $R^c$ are each independently selected from fluoro or cyano.

In a particular embodiment, x, y and z are each independently selected from 1, 2, 3, 4 or 5. In a further embodiment, x, y and z are each independently selected from 3, 4 or 5. In a further embodiment, x, y and z are all 5.

Particular examples of suitable Lewis acids include $B(C_6F_5)_3$, $B(C_6Cl_5)_3$, $B(C_6F_5)(C_6Cl_5)_2$, $B(C_6F_5)_2(C_6Cl_5)_3$, $Al(C_6F_5)_3$, $B(C_6F_4H)_3$, $BCl(C_6F_5)_2$, or $[HB(C_6F_5)_2]_n$, where n is 1 or 2.

Particular Lewis acids of interest include $C_6F_5)_3$, $B(C_6Cl_5)_3$, $B(C_6F_5)(C_6Cl_5)_2$, and $B(C_6F_5)_2(C_6Cl_5)$.

(ii) Lewis Bases

Any suitable Lewis base that can form a component of a frustrated Lewis pair that can cleave $H_2$ is encompassed by the present invention.

In an embodiment, the Lewis base is a secondary or tertiary amine group. Suitably, there are no hydrogen atoms present on the α-carbon atoms (i.e. the carbon atoms directly linked to the nitrogen atom of the amine group). The secondary or tertiary amine may be an aromatic or an aliphatic amine group.

In an embodiment, the Lewis base is an aromatic amine group of formula III shown below:

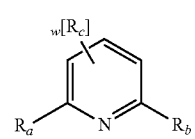

III wherein:
$R_a$, $R_b$, $R_c$ and $R_d$ are each a substituent group other than hydrogen, or a linker group to connect the compound of Formula III to a Lewis acid (e.g. —$XQ_1Q_2$, where X, $Q_1$ and $Q_2$ are as defined hereinbefore) or a solid support; and w is 0, 1, 2 or 3.

Suitably, $R_a$ and $R_b$ are selected from hydrocarbyl (especially (1-6C)alkyl, e.g. methyl or t-butyl), halo, hydroxyl, cyano, amino, NH(1-6C)alkyl, N[(1-6C)alkyl]$_2$, —S(O)$_r$-(1-6C)alkyl (where r is 0, 1 or 2), carbocyclyl (e.g. phenyl), heterocyclyl, an optionally substituted ferrocene or (0-6C)alkyl-$XQ_1Q_2$.

Suitably, $R_a$ and $R_b$ are selected from (1-6C)alkyl or phenyl.

In an embodiment, $R_a$ and $R_b$ are selected from methyl, t-butyl or phenyl.

When present, $R_c$ and $R_d$ may be any suitable ring substituent, such as, for example, halo, nitro, cyano, amino, trifluoromethyl, (1-6C)alkyl, (1-6C)alkoxy, NH(1-6C)alkyl, N[(1-6C)alkyl]$_2$, —S(O)$_r$-(1-6C)alkyl (where r is 0, 1 or 2) or aryl (e.g. phenyl).

Suitably, w is 0.

In an embodiment, the Lewis base is 2,6-dimethylpyridine or 2,6-di-t-butylpyridine.

In an alternative embodiment, the Lewis base is an aliphatic amine, particularly an aliphatic amine of the general formula IV shown below:

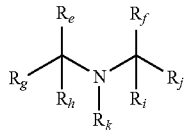

IV wherein
$R_g$, $R_h$, $R_i$ and $R_j$, are each a substituent group other than hydrogen, or one $R_g$, $R_h$, $R_i$, and $R_j$ is a linker that connects the Lewis base to a Lewis acid (e.g. —XQ$_1$Q$_2$, where X, Q$_1$ and Q$_2$ are as defined herein before) or a solid support;

$R_e$ and $R_f$ are each independently (1-6C)alkyl which may be optionally substituted with halo, nitro, cyano, amino, trifluoromethyl, (1-6C)alkyl, (1-6C)alkoxy, or —S(O)$_r$-(1-6C)alkyl (where r is 0, 1 or 2);

or $R_e$ and $R_f$ may be linked so that, together with the —C($R_g R_h$)—N($R_k$)—C($R_i R_j$)— group to which they are attached, they form a 5, 6 or 7-membered heterocyclic ring, which optionally comprises one or two additional heteroatoms selected from N, O or S, and may be optionally substituted with one or more substituent groups selected from halo, nitro, cyano, amino, trifluoromethyl, (1-6C)alkyl, (1-6C)alkoxy, or —S(O)$_r$-(1-6C)alkyl (where r is 0, 1 or 2) or a Lewis acid (e.g. —XQ$_1$Q$_2$, where X, Q$_1$ and Q$_2$ are as defined hereinbefore); and $R_k$ is hydrogen, an optionally substituted ferrocene, or a linker that connects the Lewis base to a Lewis acid (e.g. —XQ$_1$Q$_2$, where X, Q$_1$ and Q$_2$ are as defined hereinbefore) or a solid support.

In an embodiment, $R_g$, $R_h$, $R_i$ and $R_j$, are all hydrocarbyl, especially (1-6C)alkyl (e.g. methyl or t-butyl).

In an embodiment, $R_g$, $R_h$, $R_i$ and $R_j$ are all methyl.

In an embodiment, $R_e$ and $R_f$ are linked so that, together with the —C($R_g R_h$)—N($R_k$)—C($R_i R_j$)— group to which they are attached, they form a 5- or 6-membered heterocyclic ring, which optionally comprises one additional heteroatom selected from N, O or S.

In an embodiment, $R_e$ and $R_f$ are linked so that, together with the —C($R_g R_h$)—N($R_k$)—C($R_i R_j$)— group to which they are attached, they form a piperidine ring.

In an embodiment, $R_k$ is hydrogen or -(0-6C)alkyl-L-XQ$_1$Q$_2$.

A suitable Lewis base is 2,2,6,6-tetramethylpiperidine.

In an alternative embodiment, the Lewis base is a heterocyclic carbene of the general formula V:

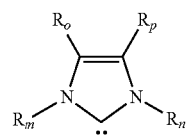

V wherein:
$R_m$ and $R_n$ are selected from hydrogen or (1-6C)alkyl;
$R_o$ and $R_p$ are both selected from hydrogen, halo, nitro, cyano, amino, trifluoromethyl, (1-6C)alkyl, (1-6C)alkoxy, NH(1-6C)alkyl, N[(1-6C)alkyl]$_2$, —S(O)$_r$-(1-6C)alkyl (where r is 0, 1 or 2) or aryl (e.g. phenyl)

or one of $R_m$, $R_n$, $R_o$ and $R_p$ is a linker that connects the Lewis base to a Lewis acid (e.g. —XQ$_1$Q$_2$, where X, Q$_1$ and Q$_2$ are as defined hereinbefore) or a solid support.

In an embodiment, $R_m$ and $R_n$, are (3-6C)alkyl, e.g. t-butyl.

In an embodiment, $R_o$ and $R_p$ are both hydrogen.

In an alternative embodiment, the Lewis base is a phosphorus containing compound of the general formula VI

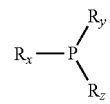

VI wherein:
$R_x$, $R_y$ and $R_z$ are each independently selected from a hydrocarbyl (especially (1-6C)alkyl, e.g. methyl or t-butyl), carbocyclyl (e.g. phenyl), heterocyclyl, or an optionally substituted ferrocene group, each of which is optionally substituted with halo, cyano, nitro, amino, aryl, heterocyclyl, (1-6C)alkyl or (1-6C)alkoxy, an optionally substituted ferrocene or a Lewis acid (e.g. —XQ$_1$Q$_2$, where X, Q$_1$ and Q$_2$ are as defined hereinbefore);

or one of $R_x$, $R_y$ and $R_z$ is a linker group that comprises a functional group capable of connecting the phosphorus atom to a solid support.

In an embodiment, $R_x$, $R_y$ and $R_z$, are each independently selected from (1-6C)alkyl, (e.g. ethyl, t-butyl) or phenyl, each of which is optionally substituted with halo, cyano, nitro, amino, (1-6C)alkyl or (1-6C)alkoxy or —XQ$_1$Q$_2$, where X, Q$_1$ and Q$_2$ are as defined hereinbefore, or an optionally substituted ferrocene.

In an embodiment, $R_x$, $R_y$ and $R_z$ are each independently selected from (1-6C)alkyl, (e.g. ethyl, t-butyl) or phenyl, each of which is optionally substituted with halo, (1-6C)alkyl or (1-6C)alkoxy or —XQ$_1$Q$_2$, where X, Q$_1$ and Q$_2$ are as defined hereinbefore.

In an embodiment, $R_x$, $R_y$ and $R_z$ are each independently selected from (1-6C)alkyl, (e.g. ethyl, t-butyl) or phenyl, each of which is optionally substituted with halo, (1-6C)alkyl or (1-6C)alkoxy or —B(C$_6$F$_5$)$_2$.

In an embodiment, $R_y$ and $R_z$ are each phenyl substituted with 1, 2 or 3 methyl and $R_x$ is ethyl, t-butyl or phenyl substituted with halo or B(C$_6$F$_5$)$_2$.

In an embodiment, $R_x$, $R_y$ and $R_z$ are each independently selected from t-butyl or phenyl substituted with 1, 2 or 3 methyl.

In the above definition of the Lewis bases, reference is made to certain groups that may function as a linker to connect the Lewis base to a Lewis acid as defined herein to form a single molecule having a Lewis base moiety and a Lewis acid moiety. The nature of the linker group is not critical as long as the Lewis acid and base moieties are spatially positioned so that they can function as a frustrated Lewis pair and heterolytically cleave hydrogen. For example, the linker may be an (1-6C)alkylene, e.g. methylene or ethylene, or (0-6C) alkylene-phenylene-, e.g. —CH$_2$-phenylene-.

Particular examples of frustrated Lewis pairs having Lewis acid and Lewis base moieties within the same molecule (and which can heterolytically cleave hydrogen) are shown below:

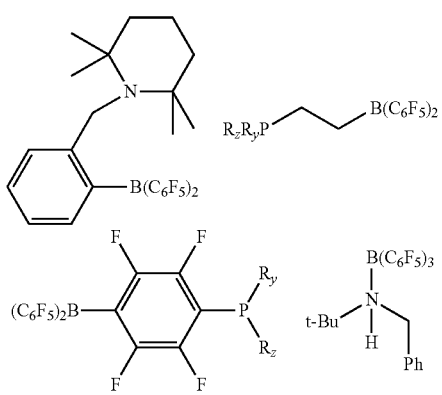

Further particular examples of frustrated Lewis pairs are $B(C_6F_5)_3$ with a Lewis base selected from:
(i) 2,6-dimethylpyridine
(ii) 2,6-di-t-butylpyridine
(iii) 2,2,6,6-tetramethylpyridine (iv)

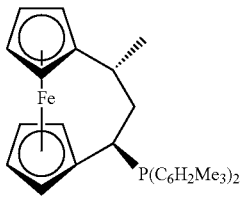

(v) $P(C_6H_4Me)_3$
(vi) $P(C_6H_2Me_3)_3$ (vii)

(viii)

(where $R_2$ is $C_6H_2Me_3$)

Methanol Synthesis

The process of the present invention is carried out in the presence of a suitable solvent. Suitable solvents include solvents that do not co-ordinate (i.e. they are non-polar). Examples include aromatic solvents such as toluene, alkanes such as hexane, and cycloalkanes.

The reaction may be conducted at any suitable temperature ranging from room temperature upwards. Temperatures of 150° C. or greater are generally preferred. A person skilled in the art will be able to select optimum temperatures for carrying out the reaction.

The reaction may also be carried out at relative low pressure (e.g. 1 to 2 atmospheres). A person skilled in the art would be readily able to optimize the pressures at which the reaction is performed.

The process may be performed as a series of discrete steps in which intermediates formed during the process are individually formed and isolated or, more preferably, the reaction may be conducted in a single step.

The methanol product formed by the process of the invention can conveniently collected by distillation.

EXAMPLES

Figure 1:
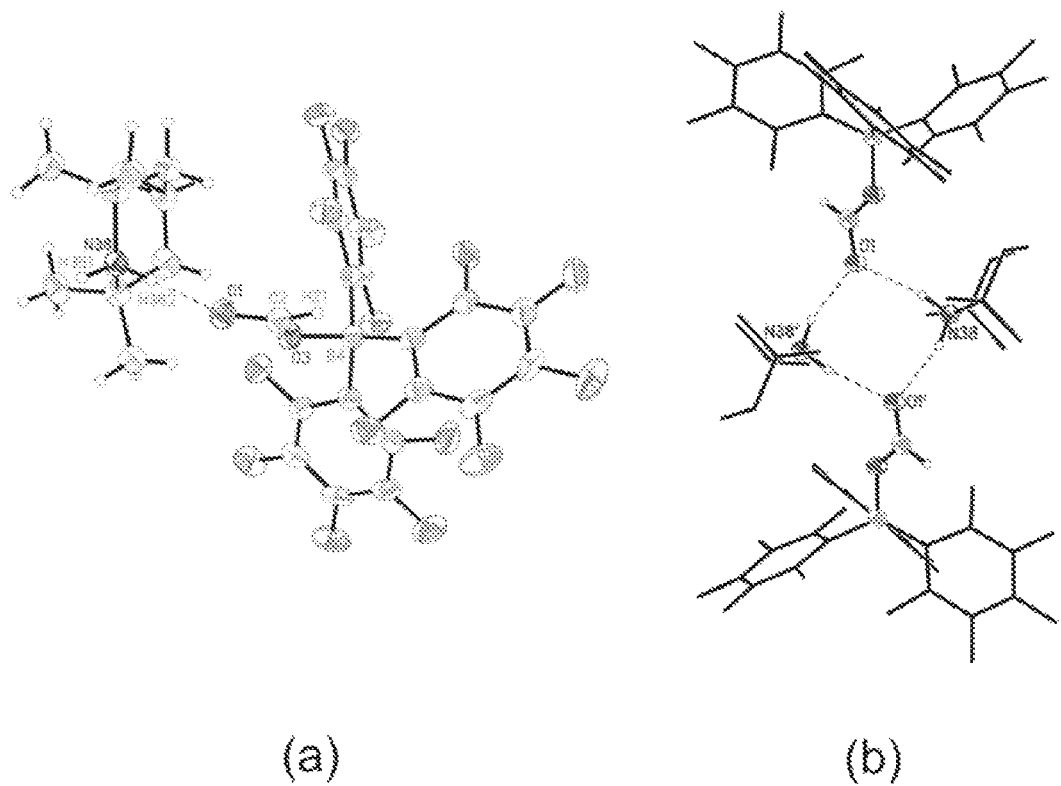
FIG. 1 shows (a) a thermal ellipsoid plot of structure of one molecule in asymmetric unit of compound 2 ([TMPH][HCO$_2$B(C$_6$F$_5$)$_3$]). Hydrogen atoms on the TMP ring have been removed for clarity, thermal ellipsoids shown at 50% probability. Selected bond lengths (Å): B4-O3 1.546(3); C2-O3 1.288(3); C2-O1 1.236(3); C2-H21 0.986; intramolecular distances for the second equivalent are statistically indistinguishable; (b) a view showing the extended H-bonding motif; N38 . . . O1 2.960(4)[2.857(4)] (H382 . . . O1 2.04[1.99]); N38 . . . O1' 2.853(4)[2.954(4)] (H381 . . . O1 1.98[2.07]) analogous distances in the second equivalent shown in square brackets.

The invention will now be described in more detail in relation to the following illustrative example.

Example 1

A Mechanistic Evaluation of the Hydrogenation of CO$_2$ to Methanol

General Procedures

Experiments were conducted on a dual-manifold gas inlet/vacuum line or in a glove-box under a nitrogen atmosphere, unless indicated otherwise.

Reaction solvents were dried using a MBraun SPS-800 solvent purification system and stored over K mirrors whilst NMR solvents were freeze-thaw degassed and stored over K ($C_7D_8$) or molecular sieves ($CD_2Cl_2$, DMSO-d$_6$).

H$_2$ (BOC) and CO$_2$ (Sigma-Aldrich) were dried via passage through a column of molecular sieves prior to use.

2,2,6,6-tetramethylpiperidine (TMP, Sigma-Aldrich) was distilled and dried over 3 Å molecular sieves.

HCO$_2$H (95% wt. %), DCO$_2$D (98% at .D) and H$^{13}$CO$_2$H (Goss Scientific, 99% at. $^{13}$C). B(C$_6$F$_5$)$_3$ (sublimed prior to use),[20] H$_2$O.B(C$_6$F$_5$)$_3$,[17c] TMP-d$_1$ (N-D)[21] and 1[7] were synthesised according to literature procedures.

The following instrumentation was used: Varian Mercury VX-Works 300 MHz for $^1$H, $^2$H, $^{13}$C, $^{19}$F (ext. CFCl$_3$ reference), $^{11}$B (ext. BF$_3$.OEt$_2$ reference) NMR spectroscopy; an Enraf-Nonius FR590KappaCCD diffractometer for X-ray diffraction; Waters GCT of EI/FI source or Bruker FT-ICR-MS Apex Qe (9.4 T, ESI in negative mode) for mass spectrometry.

GC analysis was performed on a SGE BP1 (25 m, 0.53 I.D., 5 µm film) with 50° C. hold (2.5 min) then 50° C. min$^{-1}$ ramp to 250° C. method.

Experimental

Synthesis of [TMPH][(H$^{12}$CO$_2$)B(C$_6$F$_5$)$_3$] (2)
Method A:
A 250 ml Schlenk tube was charged with 1 (0.38 mmol, 0.250 g) and toluene (30 ml) was added. The solution was freeze-thaw degassed once with $^{12}$CO$_2$ before heating to 100° C. for 12 hr in a static atmosphere of $^{12}$CO$_2$. The reaction was cooled, filtered and evaporated to give a white powder, which was washed with pentane (2×30 ml) before drying under vacuum. Yield 0.221 g (83%).

Method B:

In air, $H^{12}CO_2H$ (0.82 ml, 21.8 mmol) was added drop-wise to a stirred solution of TMP (4.00 g, 28.3 mmol) in $Et_2O$ (100 ml). The thick white precipitate was filtered, washed with $Et_2O$ (3×50 ml) and dried (12 hr) under vacuum ($10^{-3}$ mbar); yield of [TMPH][HCO2] 3.93 g (96%), stored under $N_2$. To this solid (0.98 mmol, 0.183 g) was added a solution of $B(C_6F_5)_3$ (0.98 mmol, 0.500 g) in toluene (30 ml) at room temperature with stirring in a glove-box. The mixture was filtered and the solvent stripped under vacuum. The residue was washed with pentane (2×30 ml) and vacuum dried to give 0.641 g (94%) of 2 as a white powdery solid.

$^1$H NMR ($C_7D_8$, 300 MHz): δ 8.24 (sept, 1H, $J_{HF}$=2 Hz, $HCO_2$), δ 6.46 (br, 2H, $NH_2$), δ 0.84 (m, 2H, $CH_2$), δ 0.79 (m, 4H, $CH_2$), δ 0.73 (s, 12H, $CH_3$). $^{11}$B NMR ($C_7D_8$, 128 MHz): δ -2.41 (s, br). $^{13}$C{$^1$H} NMR ($C_7D_8$, 75 MHz): δ 169.8 (s, $HCO_2$), 148.6 (dm, $^1J_{CF}$=233 Hz, ortho-$C_6F_5$), δ 140.1 (dm, $^1J_{CF}$=244 Hz, para-$C_6F_5$), δ 137.4 (dm, $^1J_{CF}$=248 Hz, meta-$C_6F_5$), δ 57.6 (s, $NC(CH_3)_2CH_2$), δ 34.7 (s, $NC(CH_3)_2CH_2$), δ 27.0 (s, $NC(CH_3)_2CH_2$), δ 15.7 (s, $NC(CH_3)_2CH_2CH_2$). Quaternary carbon of $C_6F_5$ ring was not observed.

$^{19}$F NMR ($C_7D_8$, 282.2 MHz): δ -129.0 (dd, 6F, $^3J_{FF}$=24 Hz, $^4J_{FF}$=7.6 Hz, ortho-$C_6F_5$), δ -153.1 (t, 3F, $^3J_{FF}$=21 Hz, para-$C_6F_5$), δ -159.3 (m, 6F, meta-$C_6F_5$). HRMS (ES-, m/z): for $H^{12}CO_2B(C_6F_5)_3$ Calcd: 556.9839. Found: 556.9831. R (Nujol, $cm^{-1}$): 3042 (m), 1641 (s), 1602 (m), 1517 (m), 1309 (s), 1283 (m), 1232 (w), 1219 (w), 1097 (s), 974 (s), 904 (m), 785 (w), 769 (m), 677 (w), 613 (w). IR ($CHCl_3$, $cm^{-1}$): $υ_{C=O}$ 1663. Anal. Calcd. for $C_{28}H_{21}BF_{15}NO_2$: C, 48.06; H, 3.03; N, 2.00. Found: C, 47.96; H, 2.96; N, 2.03.

Synthesis of [TMPH][($H^{13}CO_2$)$B(C_6F_5)_3$](2a)

Method B using $H^{13}CO_2H$. Yield 94%. $^1$H NMR ($C_7D_8$, 300 MHz): δ 8.24 (d, 1H, $J_{HC}$=210 Hz, $H^{13}CO_2$). $^{13}$C NMR ($C_7D_8$, 75 MHz): δ 169.9 (d, $J_{HC}$=210 Hz, $H^{13}CO_2$). HRMS (ES-, m/z): for $H^{13}CO_2B(C_6F_5)_3$ Calcd: 557.9872. Found: 557.9863. IR (Nujol, $cm^{-1}$): 3041 (m), 1646 (s), 1613 (m), 1518 (m), 1283 (m), 1097 (s), 974 (s), 901 (m), 785 (w), 769 (m), 693 (w), 612 (w). IR($CHCl_3$, $cm^{-1}$): $υ_{C=O}$ 1622

Synthesis of [TMPD($ND_2$)][($D^{12}CO_2$)$B(C_6F_5)_3$] (2b): Method B using $DCO_2D$. Yield 89%. $^2$H NMR($C_7D_8$, 46 MHz): δ 8.29 (s, br, 1D, $DCO_2$), δ 6.24 (s, br, 2D, $ND_2$), HRMS (ES-, m/z): for $D^{12}CO_2B(C_6F_5)_3$ Calcd: 557.9902. Found: 557.9911. IR (Nujol, $cm^{-1}$): 3080 (m), 1626 (s), 1517 (m), 1305 (m), 1283 (m), 1097 (s), 974 (s), 904 (m), 893 (w), 785 (w), 769 (m), 693 (w), 612 (w). IR($CHCl_3$, $cm^{-1}$): $υ_{C=O}$ 1644.

Synthesis of [TMPH][(HO)$B(C_6F_5)_3$] ($^3$)

125 ml Schlenk tube was charged with $H_2O.B(C_6F_5)_3$ (0.63 mmol, 0.330 g) and $CH_2Cl_2$ (30 ml) was added. To this a solution of TMP (0.65 mmol, 0.092 g) in $CH_2Cl_2$ (10 ml) was added drop-wise with stirring. The mixture was then filtered through Celite, the filter pad washed with $CH_2Cl_2$ (10 ml) and the solvent reduced in volume to 10 ml before layering with pentane (50 ml). After 5 days the liquid was filtered off and the large colourless crystals washed with pentane (10 ml), followed by drying under vacuum. Yield 0.349 g (83%). $^1$H NMR ($CD_2Cl_2$, 300 MHz): δ 7.15 (br, 2H, $NH_2$), δ 2.42 (sept, 1H, $J_{HF}$=2.3 Hz, OH), δ 1.74 (m, 2H, $CH_2$), δ 1.58 (m, 4H, $CH_2$), δ 1.27 (s, 12H, $CH_3$). $^{11}$B NMR ($C_7D_8$, 128 MHz): 6-3.72 (s, br). $^{13}$C{$^1$H} NMR ($CD_2Cl_2$, 75 MHz): δ 148.2 (dm, $^1J_{CF}$=236 Hz, ortho-$C_6F_5$), δ 139.3 (dm, $^1J_{CF}$=247 Hz, para-$C_6F_5$), δ 137.2 (dm, $^1J_{CF}$=251 Hz, meta-$C_6F_5$), δ 58.0 (s, $NC(CH_3)_2CH_2$), δ 36.1 (s, $NC(CH_3)_2CH_2$), δ 27.6 (s, $NC(CH_3)_2CH_2$), δ 16.3 (s, $NC(CH_3)_2CH_2CH_2$). Quaternary carbon of $C_6F_5$ ring was not observed.

$^{19}$F NMR ($CD_2Cl_2$, 282.2 MHz): δ -130.9 (d, 6F, $^3J_{FF}$=18 Hz, ortho-$C_6F_5$), 6-156.2 (t, 3F, $^3J_{FF}$=21 Hz, para-$C_6F_5$), δ -160.8 (m, 6F, meta-$C_6F_5$). HRMS (ES-, m/z): for HOB$(C_6F_5)_3$ Calcd: 528.9890. Found: 528.9887. IR (Nujol, $cm^{-1}$): 3663 (m), 3270 (m), 3048 (m), 1646 (s), 1620 (m), 1518 (m), 1278 (m), 1229 (w), 1166 (w), 1086 (s), 971 (s), 946 (s), 814 (w), 771 (w), 682 (w), 671 (w), 624 (w), 603(w). Anal. Calcd. for $C_{27}H_{21}BF_{15}NO$: C, 48.31; H, 3.15; N, 2.09. Found: C, 47.93; H, 2.96; N, 2.04.

Synthesis of [TMPH][(MeO)$B(C_6F_5)_3$](4)

To a pale yellow solution of TMP (0.48 mmol, 0.069 g) and $B(C_6F_5)_3$ (0.48 mmol, 0.250 g) in toluene (20 ml) was added anhydrous MeOH (0.096 mmol, 40 μL) with stirring. The mixture was then filtered through Celite and the solvent stripped under vacuum. The residue was then washed with pentane (2×20 ml), taken up into $CH_2Cl_2$ (40 ml) and subsequently filtered before layering with pentane (100 ml). After 5 days the supernatant was siphoned off and the colourless crystals washed with pentane (10 ml), followed by drying under vacuum. Yield 0.264 g (79%). $^1$H NMR ($CD_2Cl_2$, 300 MHz): δ 6.26 (br, 2H, $NH_2$), δ 3.12 (s, 3H, $CH_3O$), δ 1.77 (m, 2H, $CH_2$), δ 1.68 (m, 4H, $CH_2$), δ 1.41 (s, 12H, $CH_3$). $^{11}$B NMR ($CD_2Cl_2$, 128 MHz): δ -2.28 (s).$^{13}$C{$^1$H} NMR (DMSO-$d_6$, 75 MHz): δ 147.5 (dm, $^1J_{CF}$=236 Hz, ortho-$C_6F_5$), δ 137.5 (dm, $^1J_{CF}$=243 Hz, para-$C_6F_5$), δ 135.8 (dm, $^1J_{CF}$=255 Hz, meta-$C_6F_5$), δ 55.9 (s, $CH_3O$), δ 51.6 (s, $NC(CH_3)_2CH_2$), δ 34.3 (s, $NC(CH_3)_2CH_2$), δ 26.8 (s, $NC(CH_3)_2CH_2$), δ 15.7 (s, $NC(CH_3)_2CH_2CH_2$). Quaternary carbon of $C_6F_5$ ring was not observed. $^{19}$F NMR ($CD_2Cl_2$, 282.2 MHz): δ -129.3 (d, 6F, $^3J_{FF}$=20 Hz, ortho-$C_6F_5$), δ -156.5 (t, 3F, $^3J_{FF}$=20 Hz, para-$C_6F_5$), 6-161.0 (m, 6F, meta-$C_6F_5$). HRMS (ES-, m/z): for $CH_3OB(C_6F_5)_3$ Calcd: 543.0046. Found: 543.0047. IR (Nujol, $cm^{-1}$): 3248 (m), 3040 (m), 1645 (s), 1607 (m), 1517 (m), 1272 (m), 1230 (w), 1206 (w), 1090 (s), 974 (s), 917 (m), 808 (w), 765 (w), 694 (w), 667 (w), 622 (w). Anal. Calcd. for $C_{28}H_{23}BF_{15}NO$: C, 49.08; H, 3.38; N, 2.04. Found: C, 48.97; H, 3.34; N, 2.04.

Characterisation of Products of NMR Experiments:

[$C_6F_5H$]:$^1$H NMR ($C_7D_8$, 300 MHz): δ 5.80 (m, 1H). $^{19}$F NMR ($C_7D_8$, 282.2 MHz): δ -134.2 (m, 2F, ortho-$C_6F_5$), δ -149.2 (t, 1F, $^3J_{FF}$=22 Hz, para-$C_6F_5$), δ -157.4 (m, 2F, meta-$C_6F_5$). MS (FI, m/z): for $C_6F_5H$ Calcd 167.9998. Found: 167.9981.

[$CH_3OH$]: $^1$H NMR ($C_7D_8$, 300 MHz): δ 3.03 (s, 3H) GC (FID): Ret. Time 1.67 min.

[$CH_3O(C_6F_5)_2$]: $^1$H NMR ($C_7D_8$, 300 MHz): δ 3.38 (s, 3H). $^{19}$F NMR ($CD_2Cl_2$, 282.2 MHz): 6-127.6 (d, 4F, $^3J_{FF}$=17 Hz, ortho-$C_6F_5$), δ -143.8 (t, 2F, $^3J_{FF}$=20 Hz, para-$C_6F_5$), δ -155.9 (m, 4F, meta-$C_6F_5$). $^{11}$B NMR ($C_7D_8$, 128 MHz): δ 35.9 (br). MS (FI, m/z): for $C_{13}H_3OBF_{10}$ Calcd 376.0117. Found: 376.0131.

[$O_3B_3(C_6F_5)_3$]: $^{11}$B NMR ($C_7D_8$, 128 MHz): δ 26.2 (br). MS (EI, m/z): for $C_{18}F_{15}B_3O_3$ Calcd 581.9897. Found: 581.9702.

Results and Discussion

Scheme 1-Reversible reduction of $CO_2$ to formate (2) using $H_2$ activated by a frustrated Lewis acid-base pair (1). TMP denotes 2,2,6,6-tetramethylpiperidine ($C_5Me_4NH$).

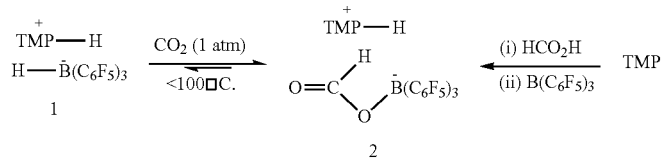

The first step in the reaction involves the heterolytic cleavage of $H_2$ using a frustrated Lewis pair. A suitable frustrated Lewis pair is 2,2,6,6-tetramethylpiperidine (TMP) and $B(C_6F_5)_3$. The reaction of $H_2$ with an equimolar ratio of 2,2,6,6-tetramethylpiperidine (TMP) and $B(C_6F_5)_3$ has been documented by Sumerin et al., to give the salt [TMPH][HB($C_6F_5)_3$](1) (Scheme 1) in which the hydrogen molecule has undergone heterolytic fission.[7].

The subsequent procedure involves the hydrogenation of $CO_2$ using 1.

The proposed mechanism by which the $CO_2$ is hydrogenated has been investigated and it has been discovered that the admission of $CO_2$ into a toluene solution of 1 at 100° C. produces the unique formato-borate complex [TMPH][$HCO_2B(C_6F_5)_3$] (2) in quantitative yield (Scheme 1). The reaction can be conveniently monitored using solution $^{19}F$ NMR.[9]

The $^1H$ NMR ($C_7D_8$) spectrum of 2 reveals a ca. 2 ppm downfield shift of the $NH_2$ protons relative to 1 and also displays a septet resonance at 8.24 ppm ($J_{HF}$=2 Hz), consistent with a through-space interaction between the formate proton and each of the six ortho-F's of the $B(C_6F_5)_3$ unit. This assignment was confirmed through selective heteronuclear $^{19}F$ decoupling experiments.[9] 2 displays a carbonyl stretch at 1662 cm$^{-1}$ in its IR spectrum ($CHCl_3$).

Single crystals suitable for X-ray diffraction were grown by slow-cooling of a toluene solution of 2 to −35° C., (FIG. 1).[10] While 2 exists as discrete ion-pairs, its B—O and C—O bond lengths more closely resemble the zwitterionic $CO_2$ adducts of the phosphine-based FLPs $tBu_3P(CO_2)B(C_6F_5)_3$ and cyclo-($Me_3C_6H_2)_2PCH_2CH_2B(C_6F_5)_2(CO_2)$ (B—O: 1.5474(15)/1.550(4); C═O: 1.2081(15)/1.209(4); C═O: 1.2988(15)/1.284(4) Å, respectively),[6]: rather than those found in [$Me_4N$][($MeCO_2)B(C_6F_5)_3$] (B—O: 1.514(2); C═O: 1.217(2); C—O: 1.324(2) Å).[11] The lengthening of the O═O bond observed for 2 is likely due to the participation of this group in H-bonding with two [TMPH] counterions, shown in FIG. 1(b). No close H-ortho-F contacts are observed in the solid-state and it is possible that the optimisation of N—H...$O_2CH$ hydrogen bonds dominates the crystal packing forces.

2 may also be synthesised in high yield by the reaction of TMP and $HCO_2H$ to give [TMPH][$HCO_2$], and then subsequent reaction with $B(C_6F_5)_3$ (Scheme 1). This convenient protocol permits the regiospecific isotopic labelling of the formate moiety using $H^{13}CO_2H$ to form [($C_5Me_4NH_2$)$H^{13}CO_2B(C_6F_5)_3$] (2a) or $DCO_2D$ in conjunction with TMP-$d_1$ (N-D) to give [($C_5Me_4ND_2$)$D^{12}CO_2B(C_6F_5)_3$] (2b), in an atom-economical manner.

Heating a solution of 2 ($C_7D_8$) above 80° C. in a sealed NMR tube under a $N_2$ atmosphere revealed that the formate complex is in equilibrium with free 002 (for 2a; 13CO2 δ=124.9 ppm in $^{13}C$ NMR) and 1; using $^{19}F$ NMR we observed 2% of 2 has dissociated to give 1.[12]

On heating 2a above 110° C. the equilibrium becomes complicated by further reactions as judged by the $^{19}F$ NMR; after 24 hr at 160° C. the production of $C_6F_5H$ and two new major species are evident, one of these displaying broad resonances overlaying those observed for the ortho- and para-F of 2a. The $^1H$ NMR spectrum is much simpler, showing a broadening and decreased intensity of the formate septet, a multiplet at 5.80 ppm ($C_6F_5H$), and the appearance of a doublet centred at 3.39 ppm ($J_{ai}$=146 Hz), characteristic of an $sp^3$-hybridised carbon environment.

Figure 2:
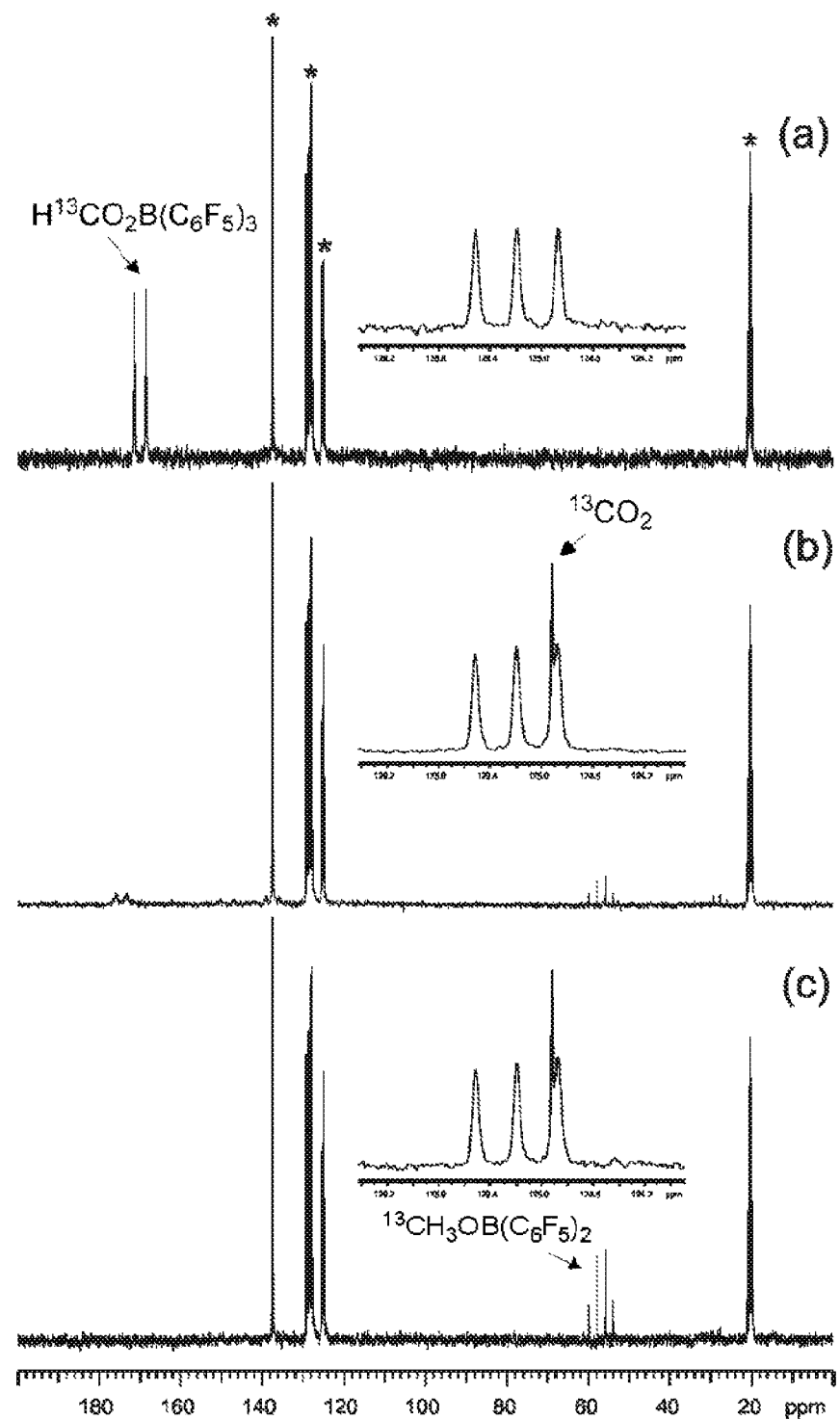
FIG. 2 shows a $^{13}$C NMR spectra of 2a after (a) 0 hr, (b) 24 hr and (c) 144 hr, at 160° C. * denotes peaks from solvent ($C_7D_8$); insets enhance region of $^{13}CO_2$ resonance.

FIG. 2 shows the time dependence of the $^{13}C$ NMR of 2a on heating at 160° C. in toluene. The formate carbon resonance of 2a (δ=169.9 ppm, $J_{CH}$=210 Hz) is seen to collapse into a broad doublet after 24 hr (δ=174.5 ppm, $J_{CH}$=230 Hz) which is concomitant with the appearance of a quartet (δ=56.8 ppm, $J_{CH}$=146 Hz) and $^{13}CO_2$, the latter two being the only species (above natural abundance $^{13}C$) observable in the spectrum after 144 hr (FIG. 2(c)); this clearly demonstrates the almost quantitative conversion of the $^{13}C$ label present in 2a. At this end-point of the reaction MS(FI) shows the homogeneous mixture to comprise of $B(C_6F_5)_3$, TMP, $C_6F_5H$ and $^{13}CH_3OB(C_6F_5)_2$ ($^{11}B$ NMR δ=35.9 ppm),[13] I all of which are supported by $^1H$, $^{19}F$, $^{13}C$ and $^{11}B$ NMR spectral data. Furthermore, use of deuterium-labelled 2b in this reaction gave $C_6F_5D$, $CD_3OB(C_6F_5)_2$ and N-deuterated TMP ($^2H$ NMR δ(ppm)=5.81, 3.30 and 1.16 respectively) as the only products incorporating deuterium. Overall this reaction represents a disproportionation of $HCO_2^-$ into $CO_2$ and $CH_3O^-$.

High-resolution mass spectrometry (ESI, -ve mode) of an aliquot of the reaction mixture after 24 hr heating at 160° C. offered great insight into the mechanism. The MS exhibited ions which could be assigned to the borate anions in 1 and 2 in addition to the $H_2O.B(C_6F_5)_3$ H-bonded anions of HOB($C_6F_5)_3$, $CH_3OB(C_6F_5)_3$, $HCO_2B(C_6F_5)_3$. Curiously, the species $(C_6F_5)_3B(HCO_2)B(C_6F_5)_3$ is also detected which could result from the reaction of $HCO_2 B(C_6F_5)_3$ with free $B(C_6F_5)_3$.

A proposed mechanism which takes into account all the experimental findings is shown in Scheme 2. The establishment of equilibrium concentrations of $CO_2$ and 1 from 2 is followed by reversible decomposition of the borohydride salt into free $H_2$, TMP and $B(C_6F_5)_3$; evidence for this process was established through $^{19}F$ NMR in which a solution of 1, when heated to 160° C., shows the presence of 17% $B(C_6F_5)_3$. Attack of this $B(C_6F_5)_3$ upon the acyl oxygen atom of 2 produces an intermediate (Scheme 2, A) which is thought to be the origin of the broad doublet seen at 174.5 ppm in the $^{13}C$ NMR spectrum; the downfield shift and line-shape corroborate an augmented electron deficiency due to the coordination of an additional bulky $B(C_6F_5)_3$ molecule around a single carbon centre. Following this, hydride reduction of the activated formate A by an equivalent of 1 leads to the formaldehyde acetal (intermediate B) and $B(C_6F_5)_3$. The instability of acetals in protic media towards an aldehyde and $H_2O$ is well-documented,[14] and in this instance the [TMPH] counterions may serve as H[+] donors; cleavage of B to $H_2CO.B(C_6F_5)_3$ (intermediate C) and 3 is by analogy. C is expected to be a potent electrophile and in the presence of 1 undergoes a final hydride reduction to form 4. The absence of any reduction products between formate and methoxide indicates that the conversion of A to B is rate-determining, and is anticipated from the necessity of crowding three large $B(C_6F_5)_3$ molecules around a hindered formate in the reduction step.

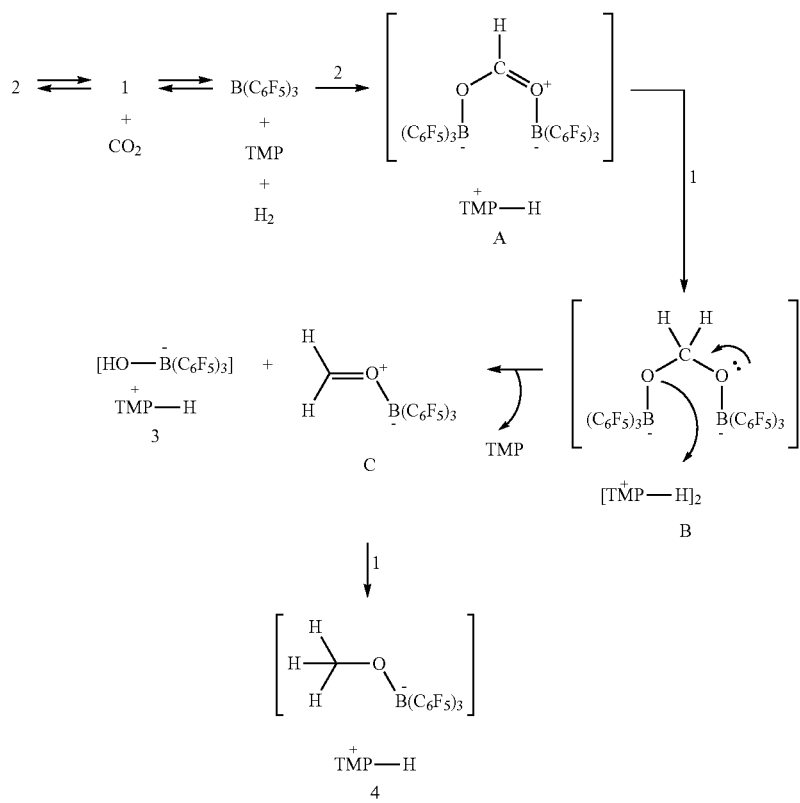

Scheme 2-Proposed mechanism for the disproportionation of 2 into 4 $CO_2$

To test the validity that 3 and 4 are formed in the reaction, these compounds were independently synthesised from either TMP and $H_2O.B(C_6F_5)_3$[15] (1:1; 3) or 1 eq. of anhydrous MeOH added to an equimolar mixture of TMP and $B(C_6F_5)_3$ (4). Heating a toluene solution (160° C.) of the latter led to the rapid production of 1 eq. of $C_6F_5H$ and $CH_3OB(C_6F_5)_2$, whilst that of the former was slower, proceeding to the boroxin $[OB(C_6F_5)]_3$[16] (presumably via $HOB(C_6F_5)_2$); all of these are identified as products in the completed reaction using $^1$H, $^{19}$F, $^{11}$B NMR and MS (EI/FI).

Scheme 3-Thermolysis of [TMPH][HOB($C_6F_5$)$_3$] (3) and [TMPH][MeOB($C_6F_5$)$_3$] (4), and production of $CH_3OH$

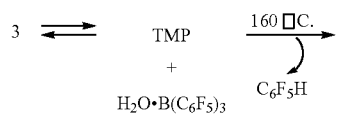

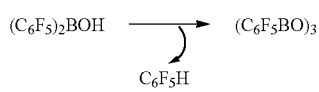

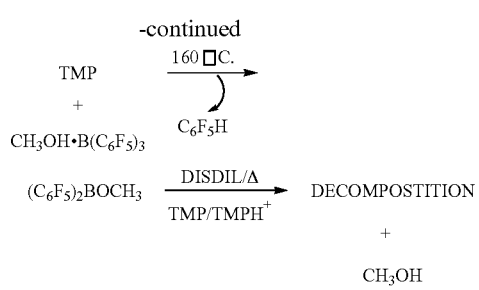

Since the only labile source of protons in the decomposition reactions of 3 and 4 is the TMPH cation, this suggests that recombination of the ion pairs to form TMP and $ROH.B(C_6F_5)_3$ (R=$CH_3$, H) must occur (Scheme 3); corroborating this hypothesis is the detection of $H_2O.B(C_6F_5)_3$ H-bonded with various anions in the MS (ES).[17] Whilst studies have shown that such adducts can dissociate to give ROH and free $B(C_6F_5)_3$,[18] at these temperatures protonation of the ipso-C on the $C_6F_5$ rings appears to be faster (yielding $ROB(C_6F_5)_2$ and $C_6F_5H$), which preclude any catalytic turnover.

Finally, addition of one equivalent of $CO_2$ to a 1:1 mixture of TMP/B($C_6F_5$)$_3$ (4 eq., excess, under $H_2$ atmosphere) in $C_7D_5$ demonstrated quantitative conversion to $CH_3OB$($C_6F_5$)$_2$ via 2, after 6 days at 160° C. Remarkably, vacuum distillation of the solvent (100° C.) led to the isolation of $CH_3OH$ (17-25% yield based on $^1H$ NMR integration against internal $Cp_2Fe$, and GC analysis) as the sole $C_1$ product, alongside $C_6F_5H$ and TMP by-products. We expect that this results from the reaction of $CH_3OB(C_6F_5)_2$ with TMP or its conjugate acid.[19]

In summary we have demonstrated the first example of the selective hydrogenation of $CO_2$ to $CH_3OH$, using an FLP-based non-metal protocol at low pressures (1-2 atm).

Example 2

Evaluation of Frustrated Lewis Pairs based on the Lewis Acids $(C_6F_5)_2B(C_6Cl_5)$ $(C_6F_5)B(C_6Cl_5)_2$ and $B(C_6Cl_5)_3$ General Techniques All air and moisture sensitive compounds were manipulated under $N_2$ using either a MBraun Unilab glovebox or using standard Schlenk line techniques on a dual manifold vacuum/nitrogen line. For the manipulation of moisture sensitive compounds, all glassware was heated to 170° C. before use. Solvents and solutions were transferred using a positive pressure of nitrogen through stainless steel or Teflon cannulae, or via plastic syringes for volumes less than 20 ml. Filtrations were performed using either glassware containing sintered glass frits or modified stainless steel cannulae fitted with glass microfibre filters.

Reaction solvents (pentane, hexane, benzene, toluene, $CH_2Cl_2$) were dried using an MBraun SPS-800 solvent purification system; the aliphatics and aromatics were stored over K mirrored ampoules. $Et_2O$ and THF were distilled from purple Na/benzophenone indicator. Dry solvents were stored in oven or flame-dried ampoules, sealed with a Rotaflo or Youngs' taps under nitrogen. $H_2$ gas (BOC) was dried via passage through a column of pre-activated 3 Å molecular sieves.

Deuterated NMR solvents were dried and freeze-thaw degassed over the appropriate drying agent: $C_6D_6$, $C_7D_5$ (K); $CD_2Cl_2$ (3 Å molecular sieves) and purchased from Goss Scientific (99.6, 99.6 and 99.8% D respectively).

$BBr_3$ (99.9%), $BCl_3$ (1.0 M in hexanes), $BF_3·OEt_2$, $C_6Cl_6$ (99.9%), $C_6F_5Br$ (99%), CuCl (>99%), Mg turnings (99.5%), $^nBuLi$ (2.5 M in hexanes), 2,2,6,6-tetramethylpiperidine (>99%), trans-crotonaldehyde (>99%) were purchased from Sigma Aldrich, 2,6-Lutidine (>98%) from Alfa Aesar and $H^{13}CO_2H$ (99% $^{13}C$) from Goss Scientific; all were used as received. The following compounds were prepared according to literature procedures, or adaptations thereof: $Zn(C_6Cl_5)_2$,[1] $CuC_6F_5$,[2] $(C_6F_5)_2BF·OEt_2$,[3] $(C_6F_5)BBr_2$,[4] and $B(C_6F_5)_3$. $B(C_6Cl_5)_2F$ was prepared as for $(C_6F_5)_2BF·OEt_2$ using $C_6Cl_5Li^5$ in place of $C_6F_5MgBr$;[2] extraction and crystallisation using toluene gave pure material (19.8%).

Solution NMR Spectroscopy

Air sensitive samples were prepared under $N_2$ atmosphere. Spectra were recorded on a 300 MHz Varian VX-Works spectrometer. The $^1H$ and $^{13}C$ chemical shifts, δ, in parts per million (ppm) are given relative to TMS (δ=0) and referenced internally to the residual proton shift in the deuterated solvent employed. $^{11}B$, $^{19}F$ and $^{31}P$ chemical shifts were referenced externally to $BF_3·OEt_2$, $CFCl_3$ and 85% $H_3PO_4$ (δ=0). Air sensitive samples were prepared inside a glovebox under nitrogen atmosphere in Youngs' adapted NMR tubes.

Mass Spectrometry

Samples were recorded by Mr. Colin Sparrow of the Chemistry Research Laboratory, University of Oxford, using a Bruker FT-ICR-MS Apex III spectrometer for EI measurements.

Infra-Red Spectroscopy

IR spectra were recorded on a Nicolet MAGNA-IR 560 FT-IR spectrometer (range 4000-400 cm$^{-1}$, resolution 0.5 cm$^{-1}$). Solution IR spectra were obtained in $CH_2Cl_2$ solvent, using a KBr cell. Solutions were injected into the cell in the glovebox and the spectra recorded immediately. Mulled samples were prepared by grinding the material into a fine powder, mulling with Nujol and the paste administered to NaCl plates which were pressed together, placed in an airtight holder and the spectra recorded immediately.

Synthesis of $(C_6F_5)_2B(C_6Cl_5)$, $(C_6F_5)B(C_6Cl_5)_2$ and $B(C_6Cl_5)_3$ (i) Synthesis of $C_6Cl_5Li$ Synthesis of $C_6Cl_5Li$ adapted from a published literature method.[22] A 250 ml Schlenk was charged with $O_6Cl_6$ (11.53 g 40.5 mmol) and left under vacuum for 20 minutes to remove any moisture. Following the addition of 150 ml $Et_2O$, the cloudy solution was cooled to −78° C. using a dry ice acetone bath. With rapid stirring, (16.5 ml, 41.3 mmol, 2.5 M) nBuLi in hexane was added by means of a syringe. The contents were allowed to warm to −10° C. until no insoluble $C_6Cl_6$ was visible, and an opaque solution of $C_6Cl_5Li$ was amber in colour. The contents were later cooled to −78° C. and stabilised by the addition of 150 ml hexane.

(ii) Synthesis of $(C_6F_5)_2B(C_6Cl_5)$ (A)

A solution of $C_6F_5MgBr$ in $Et_2O$ (50 ml, 40.5 mmol, 0.81 M) was added to a −30° C. solution of $BF_3·OEt_2$ (2.49 ml, 20.25 mmol) in $Et_2O$ (80 ml). The resulting dark brown solution was then cooled to −78° C. With rapid stirring, a solution of $C_6Cl_5Li$ (20.25 mmol) in $Et_2O$/hexane was added and the contents slowly warmed to −10° C. over the course of 1 hour. The solution was later warmed to room temperature and the crude product extracted with 150 ml hexane. Removal of the solvent gave a brownish oil found to be contaminated by small traces of $B(C_6F_5)_3$ which was removed by vacuum sublimation at 100° C. Increasing the temperature to 125° C. yielded analytically pure A as a white powdery solid (7.70 g, 12.9 mmol, 63.7%). Crystals suitable for X-ray diffraction were grown from a toluene solution slow cooled to −30° C.

$^{13}C\{^1H\}$ NMR ($CD_2Cl_2$, 75 MHz): δ 149.7 (dm, $^1J_{CF}$=251 Hz, ortho-$C_6F_5$); δ 145.9 (dm, $^1J_{CF}$=262 Hz, para-$C_6F_5$); δ 141.0 (br, ipso-$C_6Cl_5$); δ 138.0 (dm, $^1J_{CF}$=249.5 Hz, meta-$C_6F_5$); δ 135.1 (s, para-$C_6Cl_5$); δ 132.3, 131.3 (both s, meta-$C_6Cl_5$ and ortho-$C_6Cl_5$); δ 112.2 (br, ipso-$C_6F_5$).

$^{11}B$ NMR($C_7D_8$, 128 MHz): δ 63.6 (s, br)

$^{19}F$ NMR($C_7D_8$, 282.2 MHz): δ −127.3 (d, 4F, $^3J_{FF}$=22 Hz, ortho-$C_6F_5$), δ −141.0 (t, 2F, $^3J_{FF}$=23 Hz, para-$C_6F_5$), δ −159.9 (m, 4F, meta-$C_6F_5$).

HRMS (EI, m/z): for $BC_{18}C_{15}F_{10}$ Calcd: 591.8378. Found: 591.8376.

IR (Nujol, cm$^{-1}$): 1700 (m), 1653 (m), 1646 (m), 1559 (m), 1549 (m), 1521 (s), 1507 (w), 1482 (s), 1437 (m), 1382 (m), 1336 (m), 1322 (m), 1235 (w), 1167 (m), 1142 (w), 1015 (w), 979 (s), 674 (m), 668 (m), 659 (w).

Anal. Calcd. for $BC_{18}C_{15}F_{10}$: C, 36.50; H, 0.00; N, 0.00. Found: C, 36.49; H, 0.00; N, 0.00.

(iii) Synthesis of $(C_6F_5)B(C_6Cl_5)_2$ (B)

To a −78° C. solution of $(C_6F_5)BBr_2$ (4.70 g, 13.9 mmol) in hexane (20 ml), was added $C_6Cl_5Li$ (27.80 mmol) in $Et_2O$/hexane solution. The reaction mixture was gradually warmed to −10° C. and left to stir for a further hour before being warmed to room temperature. The solvent was stripped under vacuum and the compound extracted using 100 ml $CH_2Cl_2$. The solvent was later removed by vacuum and the product filtered and recrystallised from 50 ml hexane. The resultant tan solid was washed with −78° C. pentane (3×20 ml) and dried under vacuum to give a crude yield of 6.20 g (66%). Further recrystallisation from toluene (slow-cooled to −80° C.) gave a microcrystalline solid, which was washed with pentane (3×20 ml) followed by drying under vacuum to leave spectroscopically pure B as an off-white powdery solid (3.81 g 40.4%).

$^{13}C\{^1H\}$ NMR ($CD_2Cl_2$, 75 MHz): δ 149.0 (dm, $^1J_{CF}$=253 Hz, ortho-$C_6F_5$); δ 145.9 (dm, $^1J_{CF}$=261 Hz, para-$C_6F_5$); δ 138.0 (dm, $^1J_{CF}$=251 Hz, meta-$C_6F_5$); δ 139.6 (br, ipso-$C_6Cl_5$); 136.6 (s, para-$C_6Cl_5$); δ 133.0 (s, meta-$C_6Cl_5$ and ortho-$C_6Cl_5$); δ 114.5 (br, ipso-$C_6F_5$).

$^{11}B$ NMR ($C_7D_8$, 128 MHz): δ 64.1 (s, br)

$^{19}F$ NMR ($C_7D_8$, 282.2 MHz): δ −127.2 (d, 2F, $^3J_{FF}$=21 Hz, ortho-$C_6F_5$), δ −141.4 (t, 1F, $^3J_{FF}$=21 Hz, para-$C_6F_5$), δ −159.7 (m, 2F, meta-$C_6F_5$).

HRMS (EI, m/z): for $BC_{18}Cl_{10}F_5$ Calcd: 675.6844. Found: 675.6774.

IR (Nujol, $cm^{-1}$): 1700 (m), 1653 (m), 1559 (m), 1540 (w), 1521 (m), 1507 (w), 1481 (s), 1465 (s), 1394 (m), 1332 (s), 1313 (s), 1237 (m), 1190 (w), 1147 (m), 1127 (w), 1104 (w), 973 (s), 876 (w), 668 (m), 642 (w).

Anal. Calcd. for $BC_{18}Cl_{10}F_5$: C, 32.16; H, 0.00; N, 0.00. Found: C, 32.19; H, 0.02; N, 0.00.

(iv) Synthesis of $B(C_6Cl_5)_3$ (C)

To a −78° C. solution of $C_6Cl_5Li$ (31.20 mmol) in $Et_2O$/hexane was added $BCl_3$ (1.17 g, 10.0 mmol, 1.0 M) in hexane. The solution was allowed to warm to −10° C. and stirred for an hour before the cloudy orange suspension was warmed to room temperature. The solvent was removed in vacuo and the subsequent work-up performed in air. After quenching the reaction by addition of 0.5 ml $H_2O$, 250 ml of $CH_2Cl_2$ was used to extract the crude product, which was filtered through Celite and the filter pad washed with 100 ml further $CH_2Cl_2$. Solvent was removed using rotary evaporation, yielding an amber solid. Recrystallisation was performed using a minimum quantity of toluene at 100° C. followed by rapid filtration through glass wool. Slow cooling to room temperature overnight led to the formation of pale yellow crystals of C.toluene. The toluene supernatant was siphoned off and the crystals washed with pentane (2×20 ml), followed by drying overnight under vacuum ($1×10^{-3}$ mbar) to remove toluene of crystallisation; yield 3.26 g (42.2%). X-ray quality crystals were produced by a second toluene recrystallisation.

$^{13}C\{^1H\}$ NMR ($CD_2Cl_2$, 75 MHz): δ 140.6 (br, ipso-$C_6Cl_5$); 136.7 (s, para-$C_6Cl_5$); δ 135.3, 133.0 (both s, meta-$C_6Cl_5$ and ortho-$C_6Cl_5$).

$^{11}B$ NMR ($C_7D_8$, 128 MHz): δ 65.6 (s, br)

HRMS (EI, m/z): for $BC_{18}Cl_{15}$ Calcd: 751.5337. Found: 757.5177.

IR (Nujol, $cm^{-1}$): 1700 (m), 1684 (m), 1652 (m), 1558 (m), 1540 (m), 1507 (m), 1468 (s), 1334 (m), 1313 (m), 1232 (m), 1130 (w), 991 (w), 668 (m), 636 (w).

Anal. Calcd. for $BC_{18}Cl_{15}$: C, 28.74; H, 0.00; N, 0.00. Found: C, 28.85; H, 0.05; N, 0.00.

$H_2$ Equilibrium Experiments

Solid A (0.036 g, 0.061 mmol; Example 2) and TMP (0.0086 g, 0.061 mmol) were added to a Youngs' NMR tube and dissolved in $C_7D_8$. The sample was subjected to 3 freeze-pump-thaw cycles and backfilled with $H_2$ at room temperature. The tube was then placed in an oil bath at 100° C. for 12 hr. The procedure was then repeated for equivalent molar concentrations of (B)/[TMP], (A)/[Lutidine (Lut)], and (B)/[Lutidine (Lut)].

The reaction for the four frustrated Lewis pair combinations was monitored over several hours until no further changes in the $^{11}B$ and $^{19}F$ NMR signals were apparent; the NMR spectral data is shown in Table 1.

TABLE 1

$^{19}F$ and $^{11}B$ NMR spectral data for FLP reactions with $H_2$ (100° C.)

| FLP System Prior To $H_2$ | Observed Hydrides | δ($^{19}F$ NMR)/ppm$^a$ | | | δ($^{11}B$ NMR)/ppm$^b$ |
|---|---|---|---|---|---|
| | | o-F | p-F | m-F | |
| [TMP][A] | [TMPH][HB($C_6F_5$)$_3$] | −132.9 | −162.7 | −166.1 | 23.8 (d, $^1J_{BH}$ = 88 Hz) |
| | [TMPH][H(A)] | −132.3 | −163.3 | −166.5 | 18.7 (d, $^1J_{BH}$ = 85 Hz) |
| | [TMPH][H(B)] | −131.7 | −162.7 | −166.1 | 13.5 (d, $^1J_{BH}$ = 85 Hz) |
| [Lut][A] | [LutH][H(A)] | −132.3 | −163.3 | −166.5 | 18.7 (d, $^1J_{BH}$ = 85 Hz) |
| | [LutH][HB($C_6F_5$)$_2$(Lut)] | −135.5 | −159.3 | −164.6 | 7.4 (d, $^1J_{BH}$ = 100 Hz) |
| | [LutH][HB($C_6F_5$)$_3$] | −132.9 | −162.7 | −166.1 | 23.8 (d, $^1J_{BH}$ = 88 Hz) |
| | [LutH][H(A)] | −132.3 | −163.3 | −166.5 | 18.7 (d, $^1J_{BH}$ = 85 Hz) |
| [TMP][B] | [TMPH][H(B)] | −131.7 | −162.7 | −166.1 | 13.5 (d, $^1J_{BH}$ = 85 Hz) |
| [Lut][B] | [LutH][H(B)] | −131.7 | −162.7 | −166.1 | 13.5 (d, $^1J_{BH}$ = 85 Hz) |

$^a$Solvent = C7D8: reference (external): $CFCl_3$
$^b$Solvent: C7D8 reference (external): $BF_3$•$OEt_2$ Significant levels of free borane were detected in both the $^{11}B$ and $^{19}F$ NMR, demonstrating reversible activation for A and B in these FLP systems; this corroborates the Lewis acidity measurements for A, B and C which are shown to diminish with sequential $O_6Cl_5$ substitution. Detection of two additional hydride environments {[B]H$^-$ and HB($C_6F_5$)$_3$$^-$} for the [1][TMP]/$H_2$ reaction reveals that a redistribution of aryl groups is occurring for this system under these conditions; a proposed mechanism for this exchange is shown in Scheme 5. The equilibrium is likely to swing in favour of HB($C_6F_5$)$_3$ formation, since this is the hydride adduct of the strongest Lewis acid in the system; similar redistribution reactions have been observed for phenoxy-substituted boranes under FLP/$H_2$ conditions.[23]

Scheme 5: Proposed mechanism for the redistribution of aryl groups in A, catalysed by borohydride species.

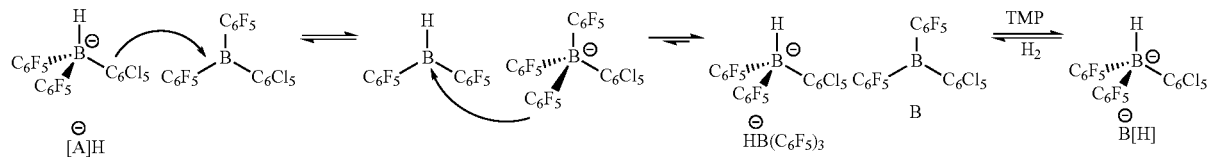

An additional hydride signal is seen in the [Lut][A]/$H_2$ experiment, downfield from the other tris(aryl)borohydride signals in the $^{11}B$ NMR; it is proposed that this is due to the presence of the lutidine adduct of the intermediate $HB(C_6F_5)_2$ shown in Scheme 5.

In contrast with the A-derived FLP systems, only a single borohydride could be observed for [TMP][B] and [Lut][B]; the enhanced bulk of a $(C_6Cl_5)_3B(C_6F_5)^-$ (Scheme 6) intermediate presumably prevents its formation and thus inhibits aryl scrambling.

Scheme 6: Non-productive pathway for the proposed aryl-scrambling mechanism (see Scheme 5) in mixtures of [B]/[B]H$^-$

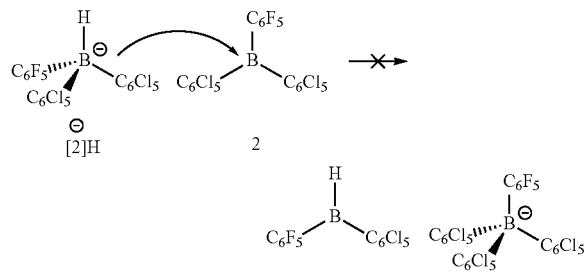

Formation of [C]H$^-$ from $B(C_6Cl_5)_3$ could only be observed at temperatures above 120° C. ($^{11}B$ NMR δ=−8.0 ppm) using TMP as the FLP partner, and was formed in much smaller amounts than in experiments involving A or B; unfortunately $^{19}F$ NMR could not be used to determine the hydride to free borane ratio in this case.

Due to the scrambling reactions observed for A, a quantitative treatment of the hydride conversion could not be obtained. For B, a conversion of 7.6% [TMPH][H(B)] and 2.5% [LutH][H(B)] were observed (using $^{19}F$ NMR integration), reflecting the difference in Lewis basicity of TMP and Lutidine.

$^{13}C$-Formate/$^{13}CO_2$ Hydrogenation Experiments

Solid [TMPH][H$^{13}CO_2$.(A)] (0.033 g, 0.042 mmol) was added to a sealable Youngs' NMR tube and dissolved in $C_7D_8$. The sample was subjected to 3 freeze-pump-thaw cycles and backfilled with $H_2$ at room temperature. The tube was then placed in a silicone oil bath held at 145° C. and reaction monitored by NMR spectroscopy until no change was observed in the intensity ratio for the $^{13}CO_2$:$^{13}CH_3O$ resonances in the $^{13}C$ NMR spectrum. The procedure was then repeated for equivalent molar solutions of [TMPH][H$^{13}CO_2$.(B)], [LutH][H$^{13}CO_2$.(A)] and [LutH][H$^{13}CO_2$.(B)].

Admission of $^{12}CO_2$ to each of the four FLP-$H_2$ reactions resulted in the formation of formato(borate) species, which were observed as new sets of resonances in the $^{19}F$ and $^{11}B$ NMR spectra. In each case the reactions were observed to be a set of equilibria for $H_2$ activation and $^{12}CO_2$ insertion, which complicated the derivation of kinetic parameters for the latter reaction. Thus to investigate the reduction of $CO_2$ with $H_2$ in a quantitative manner, the use of pre-formed formato(borate) salts permit the use of a stoichiometric equivalent of $^{13}CO_2$ to be delivered to the reaction medium; in addition the use of $^{13}C$-labelling provides an extra NMR probe using $^{13}C$ NMR to study ensuing reactions. These compounds may be synthesised in a facile manner from the reaction of $H^{13}CO_2H$ with the amine/pyridine and the respective borane[24] (Scheme 7).

Scheme 7: Reversible reduction of $CO_2$ to formato(borate) complexes and alternative synthesis from $H^{13}CO_2H$

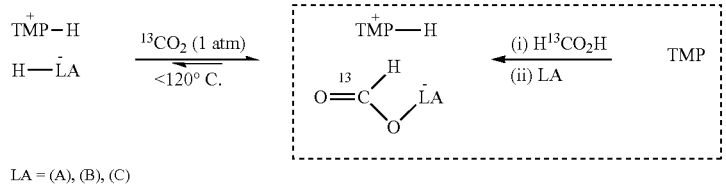

LA = (A), (B), (C)

The isolation and characterisation of (formato)borate complexes [TMPH][H$^{13}CO_2$(A)], [TMPH][H$^{13}CO_2$(B)], [LutH][H$^{13}CO_2$(A)] and [LutH][H$^{13}CO_2$(B)] were achieved in good yields. For the formate complexes of B the respective ortho- and meta-F resonances in the $^{19}F$ NMR spectrum are split and indicate hindered rotation about the formate-B bond, a result of the increased size of B over A. Furthermore the $^1H$ NMR spectrum for the $HCO_2$ proton appears as a doublet of doublets ($^1J_{CH}$=210 Hz and $J_{CF}$=5.7 Hz) showing a long-range coupling to F on the $C_6F_5$ ring.[25] For C no reaction was observed except at elevated temperatures (>80° C.), upon which decarboxylation to the FLP of C took place (presumably via $H_2$ elimination from resultant [TMPH/LutH][CH]).

Upon heating ($H_2$ atmosphere, 1 bar at 298K, sealed tube) decarboxylation occurred readily as shown by a $^{13}CO_2$ resonance ($^{13}$C NMR δ=124 ppm) and $^{19}$F signals for the borohydrides, confirming the viability of this method as an equivalent to introducing stoichiometric $^{13}$CO$_2$. Raising the temperature above 130-135° C. for the same experiments showed subsequent reduction chemistry as evidenced by the formation of $^{13}$C-coupled resonances centred around 3.3-3.6 ppm in the $^1$H NMR spectrum attributable to CH$_3$O—B species; at 145° C. the reactions were rapid and therefore this temperature was employed for all reactions. Interestingly, a repeat experiment for [TMPH][H$^{13}$CO$_2$(B(C$_6$F$_5$))$_3$] led to completion after 24 hours in comparison with 5 days previously conducted at 160° C., and it is likely that this is closer to an optimum, indicative of a mechanism involving multiple temperature-dependent equilibria.

Heating [TMPH][H$^{13}$CO$_2$(X)] (X=A, B) and [LutH][H$^{13}$CO$_2$(A)] over a period of 24 hours led to the production of three-coordinate methoxy ($^{13}$CH$_3$O—) species witnessed in the $^{19}$F, $^1$H and $^{13}$C NMR spectra. Treatment of [LutH][H$^{13}$CO$_2$(B)] under identical conditions led only to decarboxylation with concomitant formation of a mixture of [B]H$^-$ and (B).

Reactions were monitored every 2 hours until no change in the intensity ratio for $^{13}$CO$_2$ (δ=124.9 ppm) and $^{13}$CH$_3$O—B species (δ~57 ppm) by $^{13}$C NMR were observed. Termination occurred fastest (8 hours) in the case of [TMPH][H$^{13}$CO$_2$(A)] and [LutH][H$^{13}$CO$_2$(A)] with the formation of two 3-coordinate methoxy species (due to loss of C$_6$F$_5$H and C$_6$Cl$_5$H from prospective CH$_3$OH.B(C$_6$F$_5$)$_2$(C$_6$Cl$_5$) in the $^{19}$F and $^1$H NMR. Relative intensities for C$_6$F$_5$H and C$_6$Cl$_5$H were found to be in the ratio 3:1, reflecting the difference in stability and similar to that found for the decomposition experiment of A.H$_2$O.

For [TMPH][H$^{13}$CO$_2$(B)] termination was slower, occurring afters 12 hours, and also afforded two methoxy species (due to loss of C$_6$F$_5$H and C$_6$Cl$_{15}$H from prospective CH$_3$OH.B(C$_6$F$_5$)(C$_6$Cl$_5$)$_2$; however, the final C$_6$F$_5$H:C$_6$Cl$_5$H ratio approached unity. B and [B]H$^-$ are the principal F-containing species at this point of the reaction.

For the TMP-based FLP systems a trend is seen whereby the percentage of $^{13}$CH$_3$O—B increases across the series from A to B. Assuming the CO$_2$ partition coefficient remains constant between the C$_7$D$_8$ solvent and headspace of the NMR tube (i.e. the amount of observable $^{13}$CO$_2$ in solution is the same fraction of total $^{13}$CO$_2$ in the reaction throughout each reaction studied) then the TMP formato complex of B exhibits a higher yield of methoxide than that found for B(C$_6$F$_5$)$_3$. Unfortunately no free $^{13}$CH$_3$OH could be isolated, and its formation may be inhibited by performing such an experiment in a closed system, such that decomposition is forced despite dissociation occurring.

TABLE 3

Relative distribution of the $^{13}$C tag after termination

| Formato complex used | $^{13}$C Distribution/% | |
|---|---|---|
| | $^{13}$CO$_2$ | $^{13}$CH$_3$O—B |
| [TMPH][H$^{13}$CO$_2$B(C$_6$F$_5$)$_3$] | 73.4 | 26.6 |
| [TMPH][H$^{13}$CO$_2$(1)] | 34.3 | 65.7 |
| [LutH][H$^{13}$CO$_2$(1)] | 36.3 | 63.7 |
| [TMPH][H$^{13}$CO$_2$(2)] | 29.4 | 70.6 |

Remarkably the highest conversion of $^{13}$CO$_2$ to $^{13}$C-methoxide was seen for C (in situ reaction with [TMPH][$^{13}$HCO$_2$]; A strong resonance at 3.31 ppm ($^1$J$_{CH}$=146 Hz, $^{13}$CH$_3$OB(C$_6$Cl$_5$)$_2$) was observed after heating for only 2 hours; after 12 hr only trace amounts of $^{13}$CO$_2$ could be detected. For the first time a four-coordinate resonance corresponding to a hydroxy (borate) species was seen in the $^{11}$B NMR (δ=2.2 ppm; [(C)OH]$^-$), which can be generated independently through addition of H$_2$O to the FLP of TMP and C. No peak was observed for the analogous methoxy(borate) [(C)OMe]$^-$ and it is assumed that such species will eventually decompose in this system if not removed by distillation, this will be the focus of future investigations. Indeed, C$_6$Cl$_5$H grows into the spectrum at approximately the same rate as the formation of $^{13}$CH$_3$OB(C$_6$Cl$_5$)$_2$ in the initial stages of reaction, and lends support to the proposed mechanism.

For the TMP:C FLP system vacuum distillation of the solvent (100° C.) led to isolation of TMP and $^{13}$CH$_3$OH as the sole C$_1$ product [45-52% yield, two runs; $^1$H NMR δ=3.02 ppm; $^1$J$_{CH}$=145 Hz, $^{13}$C NMR=49 ppm] ascertained by $^1$H NMR integration against internal Cp$_2$Fe.

Conclusion

The Frustrated Lewis Pair systems of A-C:TMP all homogenously reduce CO$_2$ with H$_2$ to deliver a yield of MeOH. The cumulative Lewis acidity and basicity have an observed effect on the degree of activation with the stability of the formed hydroxy species appearing to increase across the series. Hydroxy species [TMPH][C.OH] can be resolved in the $^{11}$B NMR and reflects the robust nature of the Lewis Acid.

REFERENCES

[1] a) K. B. Lee, M. G. Beaver, H. S. Caram, and S. Sircar, *Ind. Eng. Chem. Res.* 2008, 47, 8048-8062; b) A. Demessence, D. M. D'Alessandro, M. L Foo, J. R. Long, *J. Am. Chem. Soc.* 2008, 131, 8048-8062; c) A. J. Fletcher, E. J. Cussen, T. J. Prior, M. J. Rosseinsky C. J. Kepert, K. M. Thomas, *J. Am. Chem. Soc.* 2001, 123, 10001-10011; d) S. Surble, F. Millange, C. Serre, T. Duren, M. Latroche, S. Bourrelly, P. L. Llewellyn, G. Ferey, *J. Am. Chem. Soc.* 2006, 128, 14889-14896; e) R. Vaidhyanathan, S. S. Iremonger, K. W. Dawson, G. K. H Shimizu, *Chem. Commun.* 2009, 5230-5232.

[2] P. G. Jessop, in *Handbook of Homogeneous Hydrogenation*, Vol. 1 (Eds: H. de Vries, K. Elsevier), WILEY-VCH, Weinheim, 2007, pp. 489-511. For reviews see: a) P. G. Jessop, T. Ikariya, R. Noyori, *Chem. Rev.* 1995, 95, 259-272; b) P. G. Jessop, F. Joo, C-C. Tai, *Coord. Chem. Rev.* 2004, 248, 2425-2442; c) T. Sakakura, J-C. Choi, H. Yasuda, *Chem. Rev.* 2007, 107, 2365-2387.

[3] a) K. Tominaga, Y. Sasaki, T. Watanabe, M. Saito, *Bull. Chem. Soc. Jpn.* 1995, 68, 2837-42; b) K. Tominaga, Y. Sasaki, M. Kawai, T. Watanabe, M. Saito, *J. Chem. Soc., Chem. Commun.* 1993, 629-31.

[4] a) C. Jiang, O. Blacque, H. Berke, *Organometallics* 2009, 28, 5233-5239; b) D. Holschumacher, C. Taouss, T. Bannenberg, C. G. Hrib, C. G. Daniliuc, P. G. Jones, M. Tamm, *Dalton Trans.* 2009, 6927-6929; c) A. Ramos, A. J. Lough, D. W. Stephan, *Chem. Commun.* 2009, 1118-1120; d) V. Sumerin, F. Schulz, M. Atsumi, C. Wang, M. Nieger, M. Leskela, T. Repo, P. Pyykko, B. Rieger, *J. Am. Chem. Soc.* 2008, 130, 14117-14119; e) G. C. Welch, D. W. Stephan, *J. Am. Chem. Soc.* 2007, 129, 1880-1881; f) P. A. Chase, D. W. Stephan, *Angew. Chem.* 2008, 120, 7543-7547; *Angew. Chem. Int. Ed.* 2008, 47, 7433-7437; g) D. Holschumacher, T. Bannenberg, C. G. Hrib, P. G. Jones, M. Tamm, *Angew. Chem.* 2008, 120, 7538-7542; *Angew. Chem. Int. Ed.* 2008, 47, 7428-7432; h) D. P. Huber, G. Kehr, K. Bergander, R. Froehlich, G. Erker, S. Tamino, Y. Ohki, K. Tatsumi, *Organometallics* 2008, 27, 5279-5284; i) G. C. Welch, R. R. S. Juan, J. D. Masuda, D. W. Stephan, *Science* 2006, 314, 1124-1126. For a review see: A. L. Kenward, W. E. Piers, *Angew. Chem.* 2007, 120, 38-42; *Angew. Chem. Int. Ed.* 2008, 47, 38-41.

[5] a) K. V. Axenov, G. Kehr, R. Froehlich, G. Erker, *Organometallics* 2009, 28, 5148-5158; b) C. M. Moemming, S. Froemel, G. Kehr, R. Froehlich, S. Grimme, G. Erker, *J. Am. Chem. Soc.* 2009, 131, 12280-12289; c) M. Dureen, D. W. Stephan, *J. Am. Chem. Soc.* 2009, 131, 8396-8397; d) M. Ullrich, K. S.-H. Kelvin, A. J. Lough, D. W. Stephan, *Chem. Commun.* 2009, 2335-2337; e) H. Wang, R. Froehlich, G. Kehr, G. Erker, *Chem. Commun.* 2008, 5966-5968; f) P. Spies, S. Schwendemann, S. Lange, G. Kehr, R. Froehlich, G. Erker, *Angew. Chem.* 2008, 120, 7654-7657; *Angew. Chem. Int. Ed.* 2008, 47, 7543-7546; g) J. S. J. McCahill, G. C. Welch, D. W. Stephan, *Angew. Chem.* 2007, 119, 8196-8199; *Angew. Chem. Int. Ed.* 2007, 46, 4968-4971; h) P. A. Chase, G. C. Welch, T. Jurca, D. W. Stephan, *Angew. Chem.* 2007, 119, 8196-8199; *Angew. Chem. Int. Ed.* 2007, 46, 8050-8053.

[6] C. M. Momming, E. Otten, G. Kehr, R. Frohlich, S. Grimme, D. W. Stephan, G. Erker, *Angew. Chem.* 2009, 121, 6770-6773; *Angew. Chem. Int. Ed.* 2009, 48, 6643-6646.

[7] V. Sumerin, F. Schulz, M. Nieger, M. Leskela, T. Repo, B. Rieger, *Angew. Chem.* 2008, 120, 6090-6092; *Angew. Chem. Int. Ed.* 2008, 47, 6001-6003.

[8] a) Even at room temperature ($CO_2$, 1 atm) this reaction proceeds to 18% conversion in 12 hours; b) No indication of reaction of 1 with CO is observable at temperatures up to 130° C.; c) Interestingly, the system [tBu$_3$PH][BH(C$_6$F$_5$)$_3$], [ref. 6(e)], does not react with $CO_2$ under the conditions successful for 1.

[9] A similar effect has been demonstrated by a $^{19}F/^{1}H$ NOE experiment: J. M. Blackwell, W. E. Piers, M. Parvez, *Org. Lett.* 2000, 2, 695-698.

[10] The structure was solved by direct methods (SIR92) and refined by full-matrix least squares (CRYSTALS). CCDC-749113 contains the supplementary crystallographic data for this paper. These data can be obtained free of charge from The Cambridge Crystallographic Data Center via www.ccdc.cam.ac.uk/data_request/cif. Crystal data for compound 2: $C_{28}H_{21}BF_{15}NO_2$, $M_r$=699.26, crystal size (mm)=0.06×0.10×0.10, triclinic, P-1, a=11.6181(1), b=14.9808(2), c=17.5277(2) Å, α=91.3525(5), β=107.8912(6), γ=100.6911(6)°, V=2842.13(6) Å$^3$, Z=4, $\rho_{calcd}$=1.634 g cm$^{-3}$, μ=0.169 mm$^{-1}$, Mo$_{K\alpha}$ radiation (λ=0.71073 Å), T=150 K, 2θ$_{max}$=27.57°, 54455 measured reflections (12965 independent, R$_{int}$=0.068), absorption correction (semi-empirical from equivalents), transmission factors 0.94/0.99, R=0.0393, wR=0.0904 refined against |F$^2$|, GOF=0.9374, [Δρ]$_{max}$ 0.44, [Δρ]$_{min}$ −0.41 e Å$^{-3}$.

[11] S. Mitu, M. C. Baird, *Can. J. Chem.* 2006, 84, 225.

[12] a) Heating a solution of [TMPH][HCO$_2$] in toluene alone results in no change, demonstrating the necessity of the borane adduct for further transformations; b) K$_{eq}$=for 2→1 has not been determined due to the uncertainty in determining the partitioning of the $CO_2$ between the liquid and gas phases.

[13] a) D. Donghi, D. Maggioni, T. Beringhelli, G. D'Alfonso, P. Mercandelli, A. Sironi, *Eur. J. Inorg. Chem.* 2008, 1645-1653; b) S. P. Lewis, J. Chai, S. Collins, T. J. J Sciarone, L. D. Henderson, C. Fan, M. Parvez, W. E. Piers, *Organometallics* 2009, 28, 249-263.

[14] a) J. Jones, in *Core Carbonyl Chemistry*, 3$^{rd}$ Edn., (Eds: S. G. Davies), OUP, Oxford, 1997; b) M. B. Smith, J. March, in *March's Advanced Organic Chemistry: Reactions, Mechanisms, and Structure*, 5$^{th}$ Edn., Wiley-Interscience, 2001, 465-468.

[15] a) C. Bergquist, T. Fillebeen, M. M. Morlok, G. Parkin, *J. Am. Chem. Soc.* 2003, 125, 6189-6199; b) T. Beringhelli, D. Maggioni, G. D'Alfonso, *Organometallics* 2001, 20, 4927-4938; c) L. H. Doerrer, M. L. H. Green, *J. Chem. Soc., Dalton Trans.* 1999, 24, 4325-4329.

[16] H.-J. Frohn, N. Y. Adonin, V. V. Bardin, V. F. Starichenko, *Z. Anorg. Allg. Chem.* 2007, 628, 2827-2833.

[17] a) A. Di Saverio, F. Focante, I. Camurati, L. Resconi, T. Beringhelli, G. D'Alfonso, D. Donghi, D. Maggioni, P. Mercandelli, A. Sironi, *Inorg. Chem.* 2005, 44, 5030-5041; b) A. A. Danopoulos, J. R. Galsworthy, M. L. H. Green, L. H. Doerrer, S. Cafferkey, M. B. Hursthouse, *Chem. Commun.* 1998, 22, 2529-2530.

[18] C. Bergquist, B. M. Bridgewater, C. J. Harlan, J. R. Norton, R. A. Friesner, G. Parkin, *J. Am. Chem. Soc.* 2000, 122, 10581-10590.

[19] NMR spectroscopy and mass spectrometry (EI) conducted on the residue after distillation to establish the identity of the B-containing products proved inconclusive, and is currently under investigation.

[20] C. Wang, G. Erker, G. Kehr, K. Wedeking, R. Froehlich, *Organometallics* 2005, 24, 4760-4773.

[21] L-L. Huang, M-H. Xu, G-Q. Lin, *J. Am. Chem. Soc.* 2006, 128, 5624-5625.

[22] Rausch, M. D.; Tibbetts, F. E.; Gordon, H. B. *J. Organomet. Chem.* 1966, 5, 493.

[23] Stephan, D. W.; Stewart, J. C.; Guerin, F.; Spence, R.; Xu, W.; Harrison, D. G. *Organometallics* 1999, 18, 1116.

[24] Ashley, A. E.; Thompson, A. L.; O'Hare, D. *Angew. Chem. Int. Ed.* 2009, 48, 9839.

[25] Blackwell, J. M.; Piers, W. E.; Parvez, M. *Org. Lett.* 2000, 2, 695.

The invention claimed is:

1. A process for the preparation of methanol comprising the steps of:
   (i) heterolytic cleavage of hydrogen by a frustrated Lewis pair comprising a Lewis acid and a Lewis base; and
   (ii) hydrogenation of $CO_2$ with the heterolytically cleaved hydrogen formed in step (i) to form methanol.

2. A process according to claim 1, wherein the Lewis acid and the Lewis base are separate molecules that together form the frustrated Lewis pair.

3. A process according to claim 1, wherein the Lewis acid and the Lewis base are separate moieties of the same molecule.

4. A process according to claim 1, wherein the Lewis acid is of the structural formula I shown below:

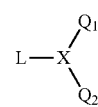

wherein:
   X is a Group 13 element;
   $Q_1$ and $Q_2$ are each independently selected from hydrocarbyl, carbocyclyl, or heterocyclyl, each of which is optionally substituted with one or more substituents selected from halo, cyano, nitro, hydroxyl, (1-6C) alkyl, (3-6C)cycloalkyl, (1-6C)alkoxy, phenyl, (1-6C)alkylphenyl, heterocyclyl, (1-6C)alkylheterocyclyl or a linker group which is capable of binding the X atom to a solid support; and L is hydrogen, halo, any one of the groups defined above for $Q_1$ or $Q_2$, or a linker group which is capable of binding the X atom to a solid support.

5. A process according to claim 4, wherein X is boron or aluminium.

6. A process according to claim 4, the Lewis acid is of the formula II shown below

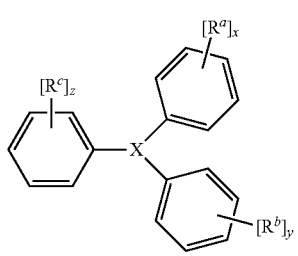

wherein:
X is a Group 13 element;
$R^a$, $R^b$ and $R^c$ are each independently selected from halo, cyano, nitro, amino, (1-6C)alkyl, (3-6C)cycloalkyl, (1-6C)alkoxy, phenyl, (1-6C)alkylphenyl; and
x, y and z are each independently selected from 0, 1, 2, 3, 4 or 5.

7. A process according to claim 6, wherein $R^a$, $R^b$ and $R^c$ are each independently selected from fluoro or cyano.

8. A process according to claim 1, wherein the Lewis acid is $B(C_6F_5)_3$, $B(C_6Cl_5)_3$, $B(C_6F_5)(C_6Cl_5)_2$, $B(C_6F_5)_2(C_6Cl_5)$, $Al(C_6F_5)_3$, $B(C_6F_4H)_3$, $BCl(C_6F_5)_2$, or $[HB(C_6F_5)_2]_n$, where n is 1 or 2.

9. A process according to claim 1, wherein the Lewis base is a compound of:

(i) formula III

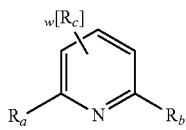

III
wherein:
$R_a$, $R_b$, $R_c$ and $R_d$ are each a substituent group other than hydrogen, or a linker group to connect the compound of Formula III to the Lewis acid or a solid support; and
w is 0, 1, 2 or 3;

(ii) formula IV

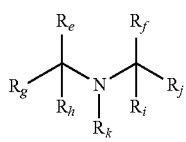

wherein
$R_g$, $R_h$, $R_i$ and $R_j$ are each a substituent group other than hydrogen, or one $R_g$, $R_e$, $R_f$ and $R_j$ is a linker that connects the Lewis base to the Lewis acid or a solid support;
$R_e$ and $R_f$ are each independently (1-6C)alkyl which may be optionally substituted with halo, nitro, cyano, amino, trifluoromethyl, (1-6C)alkyl, (1-6C)alkoxy, or —S(O)$_r$-(1-6C)alkyl (where r is 0, 1 or 2); or $R_e$ and $R_f$ may be linked so that, together with the —C($R_g R_h$)—N($R_k$)—C($R_i R_j$)—group to which they are attached, they form a 5, 6 or 7-membered heterocyclic ring, which optionally comprises one or two additional heteroatoms selected from N, O, or S, and may be optionally substituted with one or more substituent groups selected from halo, nitro, cyano, amino, trifluoromethyl, (1-6C)alkyl, (1-6C)alkoxy, or —S(O)$_r$-(1-6C)alkyl (where r is 0, 1 or 2) or the Lewis acid; and $R_k$ is hydrogen, an optionally substituted ferrocene, or a linker that connects the Lewis base to the Lewis acid or a solid support;

formula V

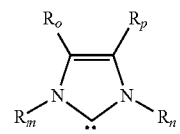

wherein:
$R_m$ and are selected from hydrogen or (1-6C)alkyl;
$R_o$ and $R_p$ are both selected from hydrogen, halo, nitro, cyano, amino, trifluoromethyl, (1-6C)alkyl, (1-6C)alkoxy, NH(1-6C)alkyl, N[(1-6C)alky]$_2$, —S(O)$_r$-(1-6C)alkyl (where r is 0, 1 or 2) or aryl (e.g. phenyl);
or one of $R_m$, $R_n$, $R_o$ and $R_p$ is a linker that connects the Lewis base to the Lewis acid or a solid support; or (iv) formula Vi

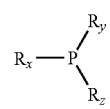

wherein:
$R_x$, $R_y$ and $R_z$, are each independently selected from a hydrocarbyl (especially (1-6C)alkyl, e.g. methyl or t-butyl), carbocyclyl (e.g. phenyl), heterocyclyl, or an optionally substituted ferrocene group, each of which is optionally substituted with halo, cyano, nitro, amino, aryl, heterocyclyl, (1-6C)alkyl or (1-6C)alkoxy, an optionally substituted ferrocene or the Lewis acid;
or one of $R_x$, $R_y$ and $R_z$ is a linker group that comprises a functional group capable of connecting the phosphorus atom to a solid support.

10. A process according to claim 1, wherein the frustrated Lewis pair is selected from:

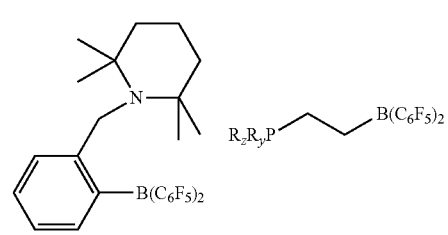

-continued

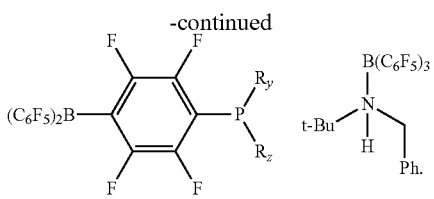 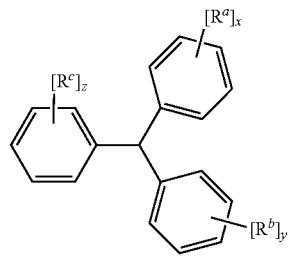

11. A process according to claim 1, wherein the frustrated Lewis pair comprises $B(C_6F_5)_3$ as the Lewis acid and the Lewis base selected from:
2,6-dimethylpyridine
2,6-di-t-butylpyridine
2,2,6,6-tetramethylpyridine

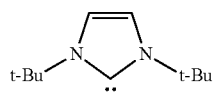

$P(C_6H_4Me)_3$
$P(C_6H_2Me_3)_3$

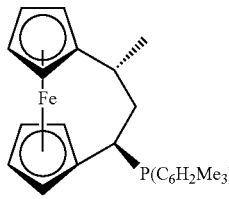 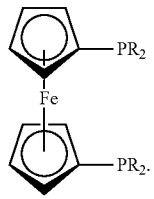

(where $R_2$ is $C_6H_2Me_3$)

12. A process according to claim 11, wherein the Lewis base is pyridine or 2,2,6,6-tetramethylpiperidine.

13. A method of heterolytically cleaving hydrogen, said method comprising the step of contacting hydrogen with a frustrated Lewis pair comprising a Lewis acid and a Lewis base,
wherein the contacting step heterolytically cleaves the hydrogen, and
wherein the hydrogen is subsequently used for the production of methanol.

14. The method according to claim 13, wherein the Lewis acid and the Lewis base are separate molecules that together form the frustrated Lewis pair.

15. The method according to claim 13, wherein the Lewis acid and the Lewis base are separate moieties of the same molecule.

16. The method according to claim 13, wherein the Lewis acid is of the structural formula I shown below:

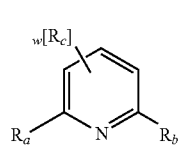

wherein:
X is a Group 13 element;
$Q_1$ and $Q_2$ are each independently selected from hydrocarbyl, carbocyclyl, or heterocyclyl, each of which is optionally substituted with one or more substituents selected from halo, cyano, nitro, hydroxyl, (1-6C) alkyl, (3-6C)cycloalkyl, (1-6C)alkoxy, phenyl, (1-6C)alkylphenyl, heterocyclyl, (1-6C)alkylhetero- cyclyl or a linker group which is capable of binding the X atom to a solid support; and
L is hydrogen, halo, any one of the groups defined above for Q1 or Q2, or a linker group which is capable of binding the X atom to a solid support.

17. The method according to claim 16, wherein the Lewis acid is of the formula II shown below

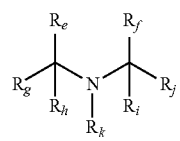

wherein:
X is a Group 13 element;
$R^a$, $R^b$ and $R^c$ are each independently selected from halo, cyano, nitro, amino, (1-6C)alkyl, (3-6C)cycloalkyl, (1-6C)alkoxy, phenyl, (1-6C)alkylphenyl; and
x, y and z are each independently selected from 0, 1, 2, 3, 4 or 5.

18. The method according to claim 13, wherein the Lewis base is a compound of:

(i) formula III

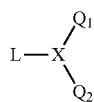

wherein:
$R_a$, $R_b$, $R_c$ and $R_d$ are each a substituent group other than hydrogen, or a linker group to connect the compound of Formula III to the Lewis acid or a solid support; and
w is 0, 1, 2 or 3;

(ii) formula IV

IV wherein
$R_g$, $R_h$, $R_i$ and $R_j$ are each a substituent group other than hydrogen, or one $R_g$,
$R_h$, $R_i$ and $R_j$ is a linker that connects the Lewis base to the Lewis acid or a solid support;
$R_e$ and $R_f$ are each independently (1-6C)alkyl which may be optionally substituted with halo, nitro, cyano, amino, trifluoromethyl, (1-6C)alkyl, (1-6C)alkoxy, or $-S(O)_r$-(1-6C)alkyl (where r is 0, 1 or 2); or
$R_e$ and $R_f$ may be linked so that, together with the $-C(R_gR_h)-N(R_k)-C(R_iR_j)-$group to which they are attached, they form a 5, 6 or 7-membered heterocyclic ring, which optionally comprises one or two additional heteroatoms selected from N, O, or S, and may be optionally substituted with one or more substituent groups selected from halo, nitro, cyano, amino, trifluoromethyl, (1-6C)alkyl, (1-6C)alkoxy, or —S(O)$_r$-(1-6C)alkyl (where r is 0, 1 or 2) or the Lewis acid; and $R_k$ is hydrogen, an optionally substituted ferrocene, or a linker that connects the Lewis base to the Lewis acid or a solid support;

(iii) formula V

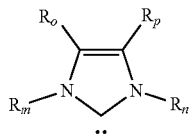

V wherein:
$R_m$ and $R_n$ are selected from hydrogen or (1-6C)alkyl;
$R_o$ and $R_p$ are both selected from hydrogen, halo, nitro, cyano, amino, trifluoromethyl, (1-6C)alkyl, (1-6C)alkoxy, NH(1-6C)alkyl, N[(1-6C)alkyl]$_2$, —S(O)$_r$-(1-6C)alkyl (where r is 0, 1 or 2) or aryl (e.g. phenyl);
or one of $R_m$, $R_n$, $R_o$ and $R_p$ is a linker that connects the Lewis base to the Lewis acid or a solid support; or (iv) formula VI

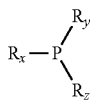

VI wherein:
$R_x$, $R_y$ and $R_z$ are each independently selected from a hydrocarbyl (especially (1-6C)alkyl, e.g. methyl or t-butyl), carbocyclyl (e.g. phenyl), heterocyclyl, or an optionally substituted ferrocene group, each of which is optionally substituted with halo, cyano, nitro, amino, aryl, heterocyclyl, (1-6C)alkyl or (1-6C)alkoxy, an optionally substituted ferrocene or the Lewis acid;

or one of Rx, Ry and Rz is a linker group that comprises a functional group capable of connecting the phosphorus atom to a solid support.

19. The method according to claim 13, wherein the frustrated Lewis pair is selected from:

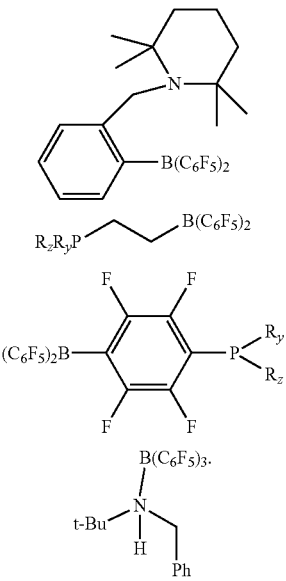

* * * * *

UNITED STATES PATENT AND TRADEMARK OFFICE
CERTIFICATE OF CORRECTION

PATENT NO. : 8,933,135 B2
APPLICATION NO. : 13/501476
DATED : January 13, 2015
INVENTOR(S) : O'Hare et al.

Page 1 of 1

It is certified that error appears in the above-identified patent and that said Letters Patent is hereby corrected as shown below:

In the Claims

In Claim 9, Column 27, Line 63, immediately after "$R_g$," and immediately before "is a linker", please delete "$R_e$, $R_f$ and $R_j$," and insert -- $R_h$, $R_i$ and $R_j$ -- therefor.

In Claim 9, Column 28, Line 27, immediately after "$R_m$ and" and immediately before "are selected", please insert -- $R_n$ -- therefor.

In Claim 9, Column 28, Line 36, immediately after "formula", please delete "Vi" and insert -- VI -- therefor.

Signed and Sealed this
Twenty-eighth Day of July, 2015

Michelle K. Lee
*Director of the United States Patent and Trademark Office*